United States Patent [19]
Stalling et al.

[11] Patent Number: 5,308,481
[45] Date of Patent: May 3, 1994

[54] CHEMICALLY BOUND FULLERENES TO RESIN AND SILICA SUPPORTS AND THEIR USE AS STATIONARY PHASES FOR CHROMATOGRAPHY

[75] Inventors: David L. Stalling; Congyuan Guo; Kenneth C. Kuo; Kevin P. Kelly; Said Saim, all of Columbia, Mo.

[73] Assignee: Analytical Bio-Chemistry Laboratories, Inc., Columbia, Mo.

[21] Appl. No.: 892,307

[22] Filed: Jun. 2, 1992

[51] Int. Cl.$^5$ .............................. B01D 15/08
[52] U.S. Cl. ........................ 210/198.2; 210/502.1; 210/635; 210/656; 502/400; 502/401; 502/402
[58] Field of Search ............ 210/635, 656, 198.2, 210/502.1; 502/400, 401, 402

[56] References Cited

U.S. PATENT DOCUMENTS

| | | | |
|---|---|---|---|
| 4,102,816 | 7/1978 | Stalling | 252/428 |
| 4,110,344 | 8/1978 | Stalling | 260/340.3 |
| 4,118,316 | 10/1973 | Talley | 210/198.2 |
| 4,303,529 | 12/1981 | Huckins | 210/635 |

OTHER PUBLICATIONS

Kroto, Nature, vol. 318, pp. 162–165, Nov. 1985.
Kratschmer, Nature, vol. 347, pp. 354–358, Sep. 1990.
Dance, J. Phys. Chem, 1991, vol. 95, No. 22, pp. 8425–8428 Oct., 1991.
Curl, Scientific American, Oct. 1991, pp. 54–62.
Bonded Stationary Phases in Chromatography, E. Grushka, ed., Ann Arbor Science Publishers, Inc., Ann Arbor, Michigan pp. 4–8, 1974.
Ajie, J. Phys. Chem, vol. 94, No. 24, pp. 8630–8633, Dec. 1990.
Haulfer, J. Phys. Chem, vol. 94, No. 24, pp. 8634–8436 Dec. 1990.

Primary Examiner—Ernest G. Therkorn

[57] ABSTRACT

The present invention relates to buckminsterfullerenes or related condensed carbon molecules covalently bonded to a polymer particle or a siliceous support particle and their use for packing media for column chromatography.

13 Claims, 28 Drawing Sheets

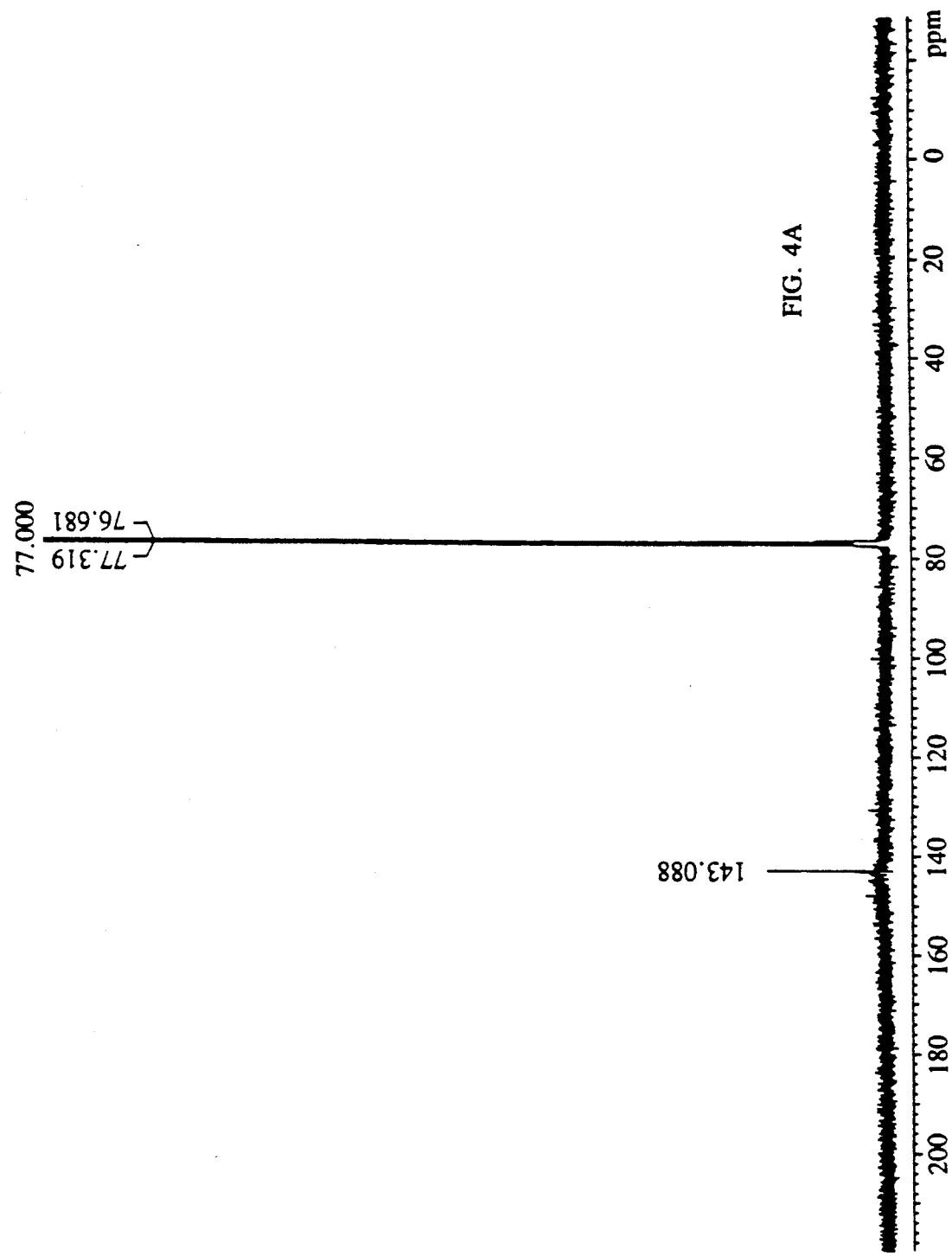

CHEMICALLY BOUND FULLERENES TO RESIN AND SILICA SUPPORTS AND THEIR USE AS STATIONARY PHASES FOR CHROMATOGRAPHY

FIELD OF THE INVENTION

The present invention relates to fullerene based materials and, more particularly, to their use as stationary phases for chromatography. The chromatography media are formed from fullerenes covalently bonded to support particles, such as polymer or silica particles.

BACKGROUND OF THE INVENTION

Although the existence of a round, hollow, geodesic sphere-shaped molecule consisting of 60 carbon atoms was first proposed by Kroto et al. in 1985 (*Nature*, Vol. 318, p. 162, 1985), it was not until 1990 that measurable amounts of this substance were prepared by Kratschmer et al. (*Nature*, Vol. 347, p. 354, 1990). This molecule was later named buckminsterfullerene or fullerene in honor of Buckminster Fuller, the inventor of the geodesic dome.

This form of carbon was obtained by resistive heating of graphite rods in an inert helium atmosphere. It is now known that fullerenes may be produced even from coal (Dance, I. G.; Fisher, K. J.; Willett, G. D.; Wilson, M. A. *J. Phys. Chem.*, 95, p. 8,425, 1991), a cheaper alternative to the graphite process.

Besides the normally occurring carbon soot contaminants such as benzene, anthracene and other polynuclear aromatics, a variety of other different carbon complexes also form, including less round, yet hollow, molecules such as $C_{32}$, $C_{50}$, $C_{70}$, $C_{84}$, and other fullerenes even larger than $C_{960}$ (Robert F. Curl and Richard E. Smalley, *Scientific American*, October 1991, p. 54–62). This new form of carbon complements the well known pyramidal shape of diamond carbon, and the hexagonal shape of graphite sheets.

By far the most abundant of all fullerenes in the raw soot are $C_{60}$ and $C_{70}$. However, fractional content of these compounds in the carbon soot obtained by any method can vary widely, and the fullerenes in the raw soot are normally recovered by either liquid extraction, sublimation or supercritical fluid extraction. Separation and recovery of essentially pure $C_{60}$ can be achieved using Envirosep-ABC columns (ABC Laboratories, Columbia, Mo.) (Stalling et al., allowed U.S. Ser. No. 07/874,473 filed on Apr. 22, 1992).

Already, graphitized carbon is widely used in chromatography columns for separation of a variety of substances including antibiotic and other hydrocarbon isomers, PCBs and pesticides. The added uniformity and ordered structure of the carbon fullerene-as opposed to amorphous carbon graphite-may open avenues for developing even more powerful adsorbent, filtration, and chromatography matrices based on carbon. However, the fullerenes need to be attached to a support and form an insoluble matrix in order to provide a stable chromatographic phase. The support may be either liquid or solid, depending on the application.

Chromatography has been in widespread use for the fractionation, separation and analysis of biological and/or ecological materials. Various chromatographic techniques in use have included adsorption chromatography, ion exchange chromatography, gel permeation chromatography, gas chromatography, paper chromatography and thin-layer chromatography. In the ecological field, particularly, several of the same or different chromatographic techniques are often required to separate the complex mixtures of organic compounds encountered in laboratory samples to be analyzed.

It has occasionally been found that certain compounds or classes of compounds, when present in unknown mixtures, interfere with the normal separation and analysis of bioaffecting agents anticipated as being components of the mixture. For example, it has been very troublesome to completely separate toxic, planar polychlorinated biphenyl (PCB) components from mixtures which include other aromatic industrial chemicals together with pesticides, herbicides, natural biological fluids and fatty tissue. Moreover, the toxic, non-planar chlorinated aromatic compounds found as pollutants in the environment, such as P,P'-DDE and other pesticides, are typically difficult to chromatographically fractionate when found in admixture with certain planar components. Such non-planar pollutants are not retained by activated charcoal or other conventional adsorbents utilized in column chromatography. Separation and subsequent analysis has, however, been achieved by means of molecular size exclusion or gel permeation polymers. These materials are cross-linked copolymer gels which function like sponges on a micro scale. The size of the gel pores is controlled by the degree of cross-linking, and only certain molecular sizes penetrate the smaller pores of the gel. Other compounds of larger molecular size penetrate larger pores or are totally excluded.

The chlorine substituted naphthalene, dibenzo-p-dioxin and dibenzofurans have been found to be very hazardous to the environment because of their high toxicity to fish and animal life at concentrations well below one ppb. These planar, polynuclear aromatic compounds are preferentially adsorbed by passage through adsorption columns containing activated charcoal powders, often in admixture with dispersive agents or filter aids such as sand, magnesia, diatomaceous earth, and glass powder. Polyurethane foam has also been employed as an inert support for the carbon material in such columns. Such adsorbents are more fully discussed in U.S. Pat. Nos. 4,102,816 and 4,110,344 which issued on Jul. 25 and Aug. 29, 1978, to Stalling et al. However, such supports, dispersive agents, and filter aids do not enhance chromatographic separation and, consequently, a minimum of two columns are normally required for analyses where both planar and non-planar aromatics are suspected to be present in the sample.

Multiple chromatographic effects have been displayed in U.S. Pat. No. 4,303,529, by Huckins et al. through the utilization of powdered carbon or charcoal in admixture with a molecular size exclusion polymer as a packing media.

SUMMARY OF THE INVENTION

It is an object of this invention to provide new, fullerene based, copolymer and inorganic media suitable for use as chromatographic materials capable of singular or multiple chromatographic effects.

It is another object of this invention to provide a packing medium for column chromatography which exhibits the separation characteristics of one or more adsorbents.

It is yet another object of this invention to provide methods of fabricating multiple effect chromatographic media for chromatography.

It is a further object of this invention to provide one-step fractionation and enrichment media for the analysis of planar and non-planar polynuclear aromatic and heterocyclic compounds, and fullerenes $C_{60}/C_{70}$.

Other objects and advantages will become apparent from the following description and the appended claims.

Briefly stated, in accordance with the aforesaid objects, it has been discovered that materials consisting essentially of a buckminsterfullerene covalently bonded with a molecular size exclusion polymer or silica particle result in new materials suitable for use as packing media for chromatography having the separation characteristics of both materials in a single configuration. The chromatographic materials of this invention find particular applicability in the purification or separation of organic compounds and in the enrichment of contaminants present in organic extracts.

BRIEF DESCRIPTION OF THE DRAWINGS

FIGS. 2A, 2B, 2C, 3, 4A, 4B, 5, 6, 7A, 7B, 8, 9A, 9B, 10A, 10B, 11A, and 11B display properties of products produced in Example 1.

The captions for the figures are as follows:

FIGS. 1A, 1B and 1C: Synthesis Reactions for Materials Useful as Chromatography Stationary Phases FIG. 2A: UV Spectrum of $C_{60}$, $C_{70}$ and the Product of Hydroboration-Bromination of $C_{60/70}$.

FIG. 2B: HPLC UV Chromatogram of 50 μl of the Product of Hydroboration-Bromination of $C_{60/70}$ Obtained by Elution with Methylene Chloride through a 50 mm long×7.8 mm I.D. Envirosep-ABC Guard Column in Series with a 300 mm Long×7.7 mm I.D. Envirosep-ABC Separation Column.

FIG. 2C: UV Spectra of the Chromatography Fractions Shown in FIG. 2B.

FIG. 3: Negative Ion Fast Atom Bombardment-Mass Spectroscopy Fragmentation Patterns of the Reaction Products of Hydroboration-Bromination of $C_{60/70}$ in Fraction 2 shown in FIG. 2B.

FIG. 4A: NMR Spectrum of a Mixture of $C_{60}$ and $C_{70}$.

FIG. 4B: NMR Spectrum of Chromatography Fraction 2 Shown in FIG. 2B.

FIG. 5: HPLC UV Chromatogram of the Product Mixture Obtained from the Synthesis Reactions in Section 1(c).

FIG. 6: UV Spectrum of Chromatography Fractions Shown in FIG. 5.

FIG. 7A: Negative Ion Fast Atom Bombardment-Mass Spectroscopy Fragmentation patterns of the reaction products in Chromatography Fraction 2 Shown in FIG. 5.

FIG. 7B: NMR Spectrum of Chromatography Fraction 2 Shown in FIG. 5.

FIG. 8: FT-IR of the Product Obtained in the Synthesis Reaction in Section 1(d) (iii).

FIGS. 9A and 9B: Magic Angle Spinning $^{13}$C-NMR Spectrum of the Product Obtained the Synthesis Reaction in Section 1(d) (iii) and its Inferred Molecular Structure.

FIGS. 10A and 10B: Magic Angle Spinning $^{13}$C-NMR Spectrum of the Product Obtained in the Synthesis Reaction in Section 1(e) and its Inferred Molecular Structure.

FIG. 11A: Adsorption of 2.5 μg of PCB in 1 ml of cyclopentane on 50 mg of Product Obtained in the Synthesis Reaction in Section 1(e). HPLC Chromatogram of the Supernatant Solution. The PCB Elutes at 13.2 min.

FIG. 12: Separation of $C_{60}$ and $C_{70}$ Fullerenes on 100 mm×1.35 mm Chromatography Columns Containing Envirosep-ABC Stationary Phase and Envirosep-ABC-$C_{60/70}$H Stationary Phase Obtained in Example 3, Respectively. Enhanced Separation is Obtained with the Envirosep-ABC-$C_{60/70}$H Stationary Phase.

FIG. 13 Separation of Polyaromatic Hydrocarbons on 100 mm×1.35 mm Chromatography Columns Containing Envirosep-ABC Stationary Phase and Envirosep-ABC-$C_{60/70}$H Stationary Phase Obtained in Example 3, Respectively. Enhanced Separation is Obtained with the Envirosep-ABC-$C_{60/70}$H Stationary Phase.

DETAILED DESCRIPTION OF THE INVENTION

Figure 1A:
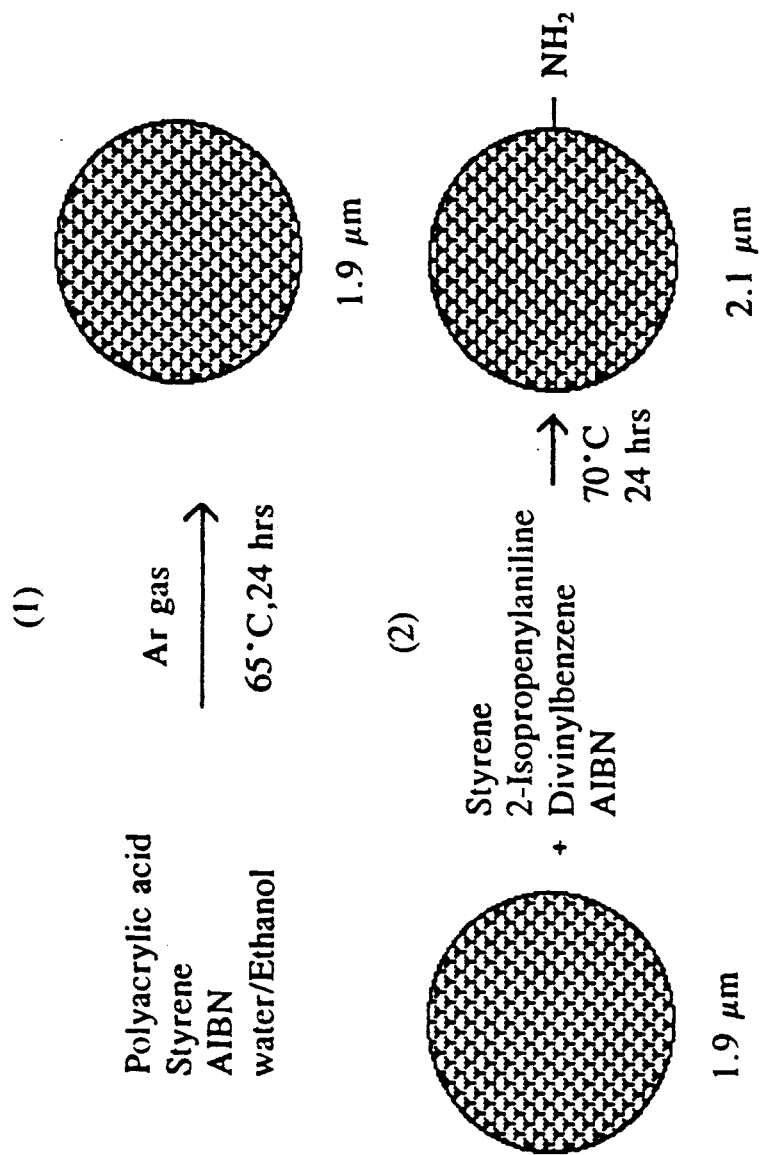
FIGS. 1A, 1B, and 1C shows the sequence of reactions according to preferred processes of the present invention.
Figure 1B:
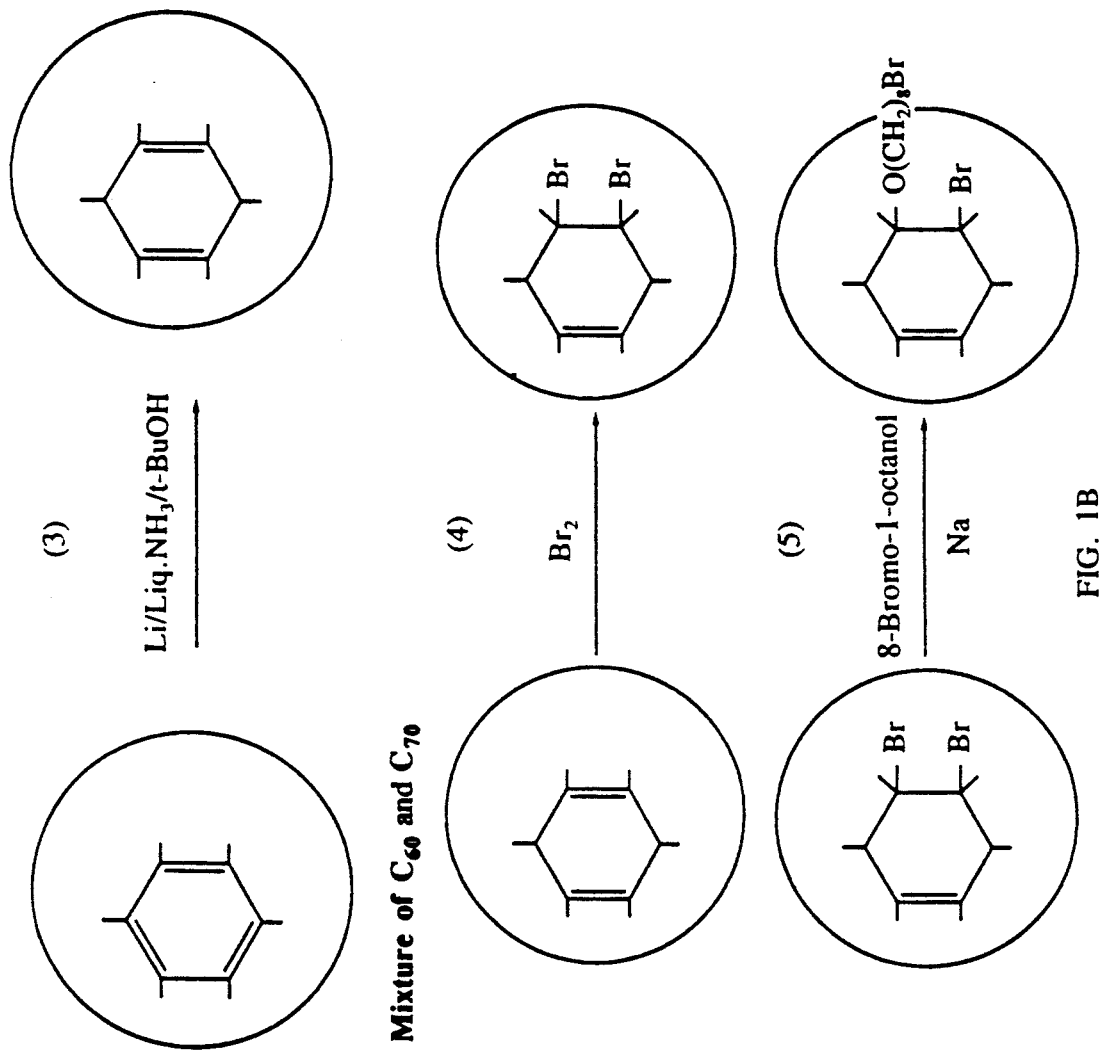

This invention relates to novel packing media for column chromatography comprising buckminsterfullerenes or related condensed carbon molecules covalently bonded to a polymer particle or a siliceous support particle. The fixation of buckminsterfullerenes onto siliceous or polymer particles and lattices creates a lattice structure that is especially useful as a chromatographic support particle. In order to effect fixation via the covalent bonding of a buckminsterfullerene with either a polymer particle or a siliceous support, the buckminsterfullerene can be either surface modified to contain a functional moiety that is reactive with a functional group on the polymer of siliceous support particle, or directly attached to aromatic polymers such as divinylbenzene polystyrene using a suitable catalyst.

The buckminsterfullerenes for use in the present invention can be essentially pure $C_{60}$, $C_{70}$, $C_{84}$ or $C_{120}$ molecules, preferably $C_{60}$ molecules, or any mixtures thereof. While the following discussion or examples may be directed to the production of covalently bonded, surface-modified $C_{60}$ or mixtures of $C_{60}/C_{70}$ molecules of buckminsterfullerene, the reactions are applicable to every form of buckminsterfullerene or to any mixtures thereof.

A mixture of $C_{60}$ and $C_{70}$ buckminsterfullerenes, hereinafter referred to as $C_{60/70}$, is either directly attached to a support particle, or is surface modified by bonding one or more reactive groups onto the $C_{60/70}$ surface matrix, prior to attaching it to a support particle. Typical reactive groups include, but are not limited to: —$CH_2X$ and —X wherein X is Cl, Br, I, or F; —OH; —$NH_2$; and —COOH. It may be desirable to provide each $C_{60/70}$ molecule with only one functional group that covalently bonds a reactive group on a polymer or silica support. Each $C_{60/70}$ molecule can contain up to 20 reactive groups and $C_{60/70}$ molecules containing one or more reactive groups are hereinafter referred to as activated buckminsterfullerenes or activated $C_{60/70}$ molecules. $C_{60/70}$ molecules having a plurality of reactive groups bond with one or more polymer or siliceous particles forming a lattice structure. The chromatographic properties of these lattice structures should have a continuum of affinities for various aromatic and other molecules, depending upon the number of carbon double bonds remaining in the activated $C_{60/70}$ molecules and linkage chemistry. The greatest chromatographic affinity for aromatic compounds is expected to be associated with a copolymer resin particle directly or spacer-linked to many $C_{60/70}$ molecules, each of which is individually linked to the surface of the polymer by a single carbon bond or other spacer chain. Linkage to the copolymer surface of many $C_{60/70}$ molecules each having several functional groups or chains (herein designated as "linked fullerene brushes"), is expected to exhibit diminished chromatographic affinity for aromatics through fewer pi-pi electron induced dipole interactions, as compared to that exhibited by materials consisting of $C_{60/70}$ directly attached to a support particle.

Reactive functional groups are substituted onto the surface of the $C_{60/70}$ molecules by any reactive carbon technology, or through the use a suitable catalyst/solvent system. The degree of substitution of the reactive functional groups onto a $C_{60/70}$ molecule is controlled by stoichiometric reactant ratios. The $C_{60/70}$ molecules can be halogenated to any required degree by suitable stoichiometric reaction with the desired halogen substituent preferably chlorine, bromine, or other halogen compounds. Halogenation of $C_{60/70}$ can also be conducted by reaction of $C_{60/70}$ molecules with metallic halides typically used in the art such as $CuCl_2$m $ZnCl_2$, $CuBr_2$, and the like.

Hydroxyl functionality can be added to $C_{60/70}$ molecules by the hydrolysis of a halide functional substituent on $C_{60/70}$. Direct linkage of $C_{60/70}$ to a PSDVB particle is obtained by reaction using $AlCl_3$ and a suitable solvent such as $CS_2$. The polymer and the siliceous supports are defined as support particles and may be solid or porous, preferably of the porous particle types that are known for use as adsorbents in chromatographic columns such as porous molecular size exclusion polymer particles and siliceous support particles. The molecular size exclusion polymeric and siliceous support particles useful in the practice of this invention are widely used in liquid chromatography, particularly in gel permeation chromatography (also known as gel filtration), for synthetic polymer fractionation requiring organic solvents. Separation primarily depends on the hydrodynamic volume or effective molecular sizes of the solutes in the solution being analyzed and the availability of comparable or larger pore sizes in the polymeric packing material contained in the column. The polarity of the solute molecules appears to be of minor importance. In operation, the smaller solute molecules pass comparatively slowly down the column because they are continually entering and exiting the pores of the polymeric or siliceous packing material, resulting in a longer effective path length. The larger molecules are totally excluded from the pores so they travel more rapidly and emerge first from the column. However, both non-porous polymers and siliceous supports are considered to be support particles within the scope of the invention. The use of porous support particles allows the bound $C_{60/70}$ support particle structures to display multiple chromatographic effects. The use of solid support particles restricts these structures to singular chromatographic effects. Support particles can have any diameter effective for providing chromatographic effects such as a diameter ranging from about 1 to 100 microns, preferably from 1 to 10.0. Generally porous support particles have a pore size varying from 10 to 50,000 Å, preferably 50 to 5,000 Å, although any pore size for providing chromatographic effects is suitable.

A wide variety of polymers and inorganic substrates have been utilized to effect molecular size separation in chromatographic columns. The most common polymers for use as molecular size exclusive polymers are cross-linked polystyrenes. Preferred polymers for use in this invention are particles formed from a comonomer system including a vinyl aromatic monomer, such as styrene, and a conjugated diolefin monomer, such as 1,3-butadiene, cross-linked with a divinyl aromatic monomer, such as divinylbenzene. Additional monomers are incorporated into the comonomer system to provide the subsequently produced copolymer with functional groups that are reactive either directly or with pendant functional groups on the activated buckminsterfullerene.

Particles useful as support particles in the present invention are prepared by common techniques known in the art such as by dispersion or suspension polymerization. In suspension polymerization of a mixture of an initiator and a monomer, the monomer is dispersed in water. A dispersing agent is incorporated into the mixture to stabilize the suspension formed. Suspension polymerization generally uses some type of agent to keep the monomer globules dispersed throughout the reaction mixture in order to avoid coalescence and agglomeration of the polymer. A dispersing agent or suspension stabilizer may control the particle size and shape. A variety of dispersing agents including water-insoluble, finely divided, inorganic materials and organic materials, depending upon the monomers to be polymerized, have been used as dispersing agents. Thus, for example: talc; barium, calcium and magnesium carbonates, silicates, phosphates and sulfates; as well as polyvinyl alcohol, tragacanth gum, salts of styrene-maleic anhydride copolymers, vinyl acetate-maleic anhydride copolymers and their salts, starch, gelatin, pectin, alginates, methyl cellulose, carboxymethylcellulose, bentonite, limestone and alumina have been used as dispersing agents. A major advantage of suspension polymerization is that the polymeric products are obtained in the form of small beads, useful as support particles in the present invention, which are easily filtered, washed and dried. For reasons of cost, non-reactivity and environmental considerations, water is a much more desirable diluent and heat transfer medium than most organic solvents.

Vinyl aromatic monomers useful in production of polymeric or support particles include one or more vinyl aryl and alpha-vinyl aryl compounds such as styrene, alpha-methyl styrene, vinyl toluene, vinyl naphthalene, alpha-methylvinyl toluene, vinyl biphenyl, and corresponding compounds in which the aromatic nucleus may have other alkyl derivatives up to a total of 8 carbon atoms. Suitable copolymerizable conjugated diolefin monomers include one or more 1,3-dienes selected from the group of 1,3-butadiene; 2-methyl-1,3-butadiene (isoprene); 1,3-pentadiene (piperylene); 2,3-dimethyl-1,3-butadiene; 2-ethyl-1,3-butadiene; 4-methyl-1,3-pentadiene; 2-methyl-1,3-pentadiene; 2,4-hexadiene; 4-methyl-1,3-hexadiene; 2-methyl-2,4-hexadiene; 2,4-dimethyl-1,3-pentadiene; 2-isopropyl-1,3-butadiene; 2-amyl-1,3-butadiene; 1,1-dimethyl-3-tertiary-butyl-1,3-butadiene; 2-neopentyl-1,3-butadiene; and 2,3-diphenyl-1,3-butadiene and the like.

Polymeric support particles can be prepared containing styrene or styrene-containing copolymers including carboxylated polystyrene, carboxylated polystyrene-butadiene copolymers, and styrene-acrylamide, acrylonitrile-butadiene-styrene, or styrene-methacrylate copolymers.

It has also been found that polymer particles having a core-shell construction are particularly suitable for the covalent fixation of buckminsterfullerene molecules for use as chromatographic supports. The core of the core-shell particles is not fundamentally critical, as long as the condition is met that the resulting latex particles have a stable form, i.e. exhibit sufficient rigidity. It is in the nature of the core-shell construction that undesirable interactions with the core material are weak, so that a relatively large selection of materials exists.

Accordingly, it is possible to construct the core material from such monomers or comonomers from derivatives of methacrylic acid and of acrylic acid. These "hard" copolymers are, for example copolymers comprising methyl methacrylate, butyl methacrylate, and methyl acrylate, inter alia, and need not be crosslinked. Monomers of the styrene type can also be employed in the core of the latex, e.g. styrene, vinyltoluene or divinylbenzene. If the glass transition temperature, $T_\lambda$ max, of the core polymer is clearly below 0° C., i.e. if the polymer is intrinsically "soft", then the use of at least 1 percent of a crosslinking agent is recommended, e.g. glycol dimethacrylate, divinylbenzene, etc. A preferred core material for use in the present invention is prepared by copolymerizing polyacrylic acid and styrene.

The shell of the core-shell polymer particle preferably is made from a material capable of being swollen by water. The shell material should be hydrophilic to such a high degree, as a result of its composition, that it would be at least partially soluble in water if it were not anchored to the core material and/or if it were not crosslinked. Thus, the shell can also be crosslinked within itself. The solution of the shell of the latex particle in surrounding water is thus hindered by bonding to the particle core, e.g. as a result of grafting and/or crosslinking.

Further, the shell polymer has functional groups which are necessary for the covalent fixation of underivatized or activated buckminsterfullerene structures. For example, such functional groups, react in aqueous or non-aqueous solution with activated buckminsterfullerene or with an intermediate reactive spacer compounds. The choice of the functional groups on the shell or the support particles takes into consideration that the material to be fixed, namely an activated buckminsterfullerene, was surface modified to contain at least one reactive group.

The polymer of said shell typically should have:

(a) from 5.0 to 100 percent, by total weight of the polymer material of said shell, of a combination of at least one monomer having a functional group and at least one hydrophilic monomer A, but the content of said monomer having a functional group being at least 0.1 percent;

(b) from 0 to 95 percent by weight of at least one non-hydrophilic monomer B; and (c) from 0 to 30, preferably 0.1 to 20 percent by weight of at least one crosslinking monomer Y.

Each functional group on the shell that can react with one of the activated buckminsterfullerenes is a reactive group. Preferably, reactive groups are selected from the polymer particle reactive groups including a sulfonic acid halide group, an acid group, a isothiocyanate group, an isocyanate group, an activated ester, or a thiocarbonyldioxy, carbonylimidoyldioxy, haloethoxy, haloacetoxy, oxirano, aziridino, formyl, keto, acryloyl, or anhydride, hydroxyl, amino, halo groups, or the like.

As sulfonic acid halides, the chloride and bromide are preferably used. The fluoro, chloro, and bromo compounds can be used as haloacetoxy compounds. As ester components, the activated esters of imido compounds (such as those of N-hydroxysuccinimide or of N-hydroxyphthalimide), of phenols activated with electron-attracting groups (such as halophenols like trichlorophenol, or of nitrophenols), or of heterocyclic lactams such as pyrrolidone can be used. Oxirano, hydroxyl, isothiocyanato, activated carboxylic acid ester, carboxylic acid, and amino groups are particularly preferred.

For example, as the hydrophilic component A, substituted methacrylamides and acrylamides of the general formula

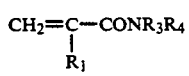

can be used, wherein $R_1$ is hydrogen or methyl and $R_3$ and $R_4$, independently of each other, can be hydrogen and/or alkyl having 1 to 4 carbon atoms, that is unsubstituted amides as well as amides formed with primary and secondary amines. Methacrylamide, N-methyl- or N-isopropyl- or N-butyl-methacrylamide, and N,N-dimethyl-methacrylamide and the corresponding acrylamides should be especially mentioned, as well as methacrylic acid morpholide (a particular case in which $R_3$ and $R_4$, together with the nitrogen atom to which they are attached, form a ring), and N-vinyl-2-pyrrolidone.

Further, 2-(methylsulfinyl)ethyl acrylate as well as N-[2-(methylsulfinyl)ethyl]acrylamide are included within monomer type A. Polymerizable acids such as acrylic acid, methacrylic acid, itaconic acid, or maleic acid can also be incorporated as hydrophilic groups in the shell as can polymerizable tertiary amines like N,N-dimethylamino-2-ethylmethacrylamide or methacrylic acid esters or N,N-dimethylamino-3-propylmethacrylamide or methacrylic acid esters. To avoid imparting a net electrical charge to the latex particles, these acidic or basic groups should always be simultaneously present (e.g. methacrylic acid and N,N-dimethylamino-2-ethylmeth acrylate), so that the particles are substantially electrically neutral. Other hydrophilic polymers include polymers of alkylene oxides such as ethylene oxide, propylene or their mixtures.

As monomers of type B, those monomers are employed which are either insoluble in water or have at most limited solubility in water, whereby the qualitative and quantitative amount is so measured that the hardness criterion for the resulting polymer mentioned earlier is satisfied.

Typical of these monomers are:

(a) esters of acrylic acid and/or of methacrylic acid with alcohols having from 1 to 20 carbon atoms, particularly the methyl, ethyl, propyl, and butyl esters of methacrylic acid, as well as the methyl, ethyl, propyl, butyl, and 2-ethylhexyl esters of acrylic acid, and (b) polymerizable monomers of the vinyl acetate type, particularly vinyl acetate, vinyl propionate, vinyl butyrate, and vinyl isobutyrate.

It is understood that the so-called "soft" monomers of type B can only be present in subordinate amounts, generally less than 50 percent by weight of the polymer of the shell.

The amount of the crosslinking agent Y is so measured that a washing away of the shell is no longer possible: as a rule at least 0.1 percent by weight of the material is necessary for this purpose. Larger amounts of crosslinking agent are in no way interfering, so that as a rule amounts from 0.1 to 20 percent, particularly from 1 to 10 percent by weight, are used.

From a chemical viewpoint, Y can be any diene or multifunctional acrylate or methacrylate, e.g. glycol dimethacrylate, butanediol diacrylate, triethyleneglycol dimethacrylate, tetraethyleneglycol diacrylate, and pentaerythritol tetraacrylate. Not all functional OH groups of the polyol which is used as a basis for the crosslinking agent need be esterified with polymerizable acids (e.g. pentaerythritol dimethacrylate has two free OH groups), so that these crosslinking agents also can exhibit a thoroughly hydrophilic character. A further example for a hydrophilic crosslinking agent is N,N-methylene-bis-(methacrylamide).

The preparation of core-shell polymer particles can take place following techniques known in the art as displayed in U.S. Pat. No. 4,829,401 to Kraemer et al., which is herein incorporated by reference.

The monomer systems identified for the production of the shell polymer can also be independently utilized to form the total polymer particle to be used as a support particle in the present invention.

A preferred support particle is prepared by the aqueous suspension polymerization of a monounsaturated, hydroxy substituted, liquid acrylic monomer and a cross-linking agent in the presence of 0.1 to 5% of a water soluble polymeric suspending agent. Polymerization proceeds at a temperature above about 50° C., preferably 70° C. to reflux in the presence or absence of a catalyst. The preferred monomer is a hydroxy alkyl substituted acrylate or acrylamide or an amino alkyl substituted acrylate. Representative monomers may be selected from compounds of the formula:

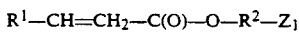

$$R^1-CH=CH_2-C(O)-O-R^2-Z_1$$

where $R^1$ is hydrogen or lower alkyl of 1-8 carbon atoms, $R^2$ is alkylene of 1-12 carbon atoms, $Z_1$ is OH or $-N(R_3)R_4$ where $R_3$ or $R^4$ Fe are H, lower alkyl or lower alkoxy, hydroxyethylmethacrylate, hydroxypropyl methacrylate, dimethylaminoethyl methacrylate and 2-aminoethyl methacrylate which are readily available commercially. Minor amounts of 1-35%, preferably 10-25%, of a compatible comonomer such as a lower alkyl methacrylate, acrylic or methacrylic acid, styrene or vinyl toluene may be added to the polymerizable mixture.

The cross-linking agent is preferably present in the polymerizable mixture in an amount from 0.1 to 30% such as diene or a triene capable of addition polymerization with the unsaturated group of the monomer or a low molecular weight liquid polyvinyl compounds such as ethylene dimethacrylate, divinylbenzene, trimethylol propane trimethacrylate and N,N'-methylene-bis-acrylamide.

The monomers are diluted in aqueous medium at a level of from 5 to 50% by weight. The aqueous medium comprises water and the hydrophilic component A. These hydrophilic polymers may be present in an amount as low as 0.05 weight percent. Amounts above 5% are believed unnecessary and require added time and effort to remove the polymer from the final beads.

A particularly preferable support particle is prepared by polymerization of 80 to 99 weight percent of a vinylaromatic monomer such as styrene, 0.1 to 5 percent by weight of a divinyl aromatic monomer and 0.1 to 5 percent by weight of an amino functional olefinic monomer such as 2-isopropenylaniline. This preferred polymer formulation can be surface coated onto a polymer bead such as displayed in FIG. 1A, reactions 1 and 2.

Uniformly shaped and sized beads generally having a molecular weight from 300,000 to 10,000,000, can be produced in an aqueous medium containing polyethers. The polymerization proceeds without catalyst and without stirring, with application of heat to the mixture at a temperature of from 70° C. to reflux, generally about 100° C., or with application of high energy radiation capable of generating free radicals and initiating polymerization and forming cross-linking bonds between olefinic groups. Polymerization proceeds by application of 0.05 to 1.0 megarads of radiation from a cobalt gamma source at a temperature of 0° to 70° C. The reaction is preferably conducted under oxygen excluding conditions, generally by applying vacuum to the reaction vessel or by displacing the head space with an inert gas such as nitrogen. A free radical catalyst such as ammonium persulfate and additional agents such as other suspending or emulsifying agents may be present in the polymerizable mixture.

After polymerization has proceeded to completion, the polymerization mixture is diluted with hot water and filtered and washed with boiling water to remove the polyether. The dry material in over 90% yield is in the form of separate round beads or agglomerates of beads. Agglomerates, if present, are subdivided into beads mechanically by dispersion in a non-solvent liquid, crushing or grinding. Preferably, beads are uniformly sized and at least 80% and preferably at least 90% of the beads are of a uniform diameter less than 10 microns. The cross-linked porous beads are insoluble and swellable in water and are insoluble in common inorganic and organic solvents.

Siliceous supports can also be employed for immobilization or fixation of activated buckminsterfullerenes. Typically, porous or non-porous silica particles can be surface modified to contain functional groups that are reactive with the reactive groups of the activated buckminsterfullerene.

Any solid or controlled porosity siliceous support can be treated with a silane compound in accordance with the procedure set forth in *Bonded Stationary Phases* in Chromatography, E. Grushka, ed., Ann Arbor Science Publishers, Inc., Ann Arbor, Mich., p. 4-8, 1974. The mechanism of this reaction involves the condensation reaction of an ester, ether, halide or silanol functional group on the silane with the silanols on the silica surface. This reaction is carried out in aqueous solution and at elevated temperatures in order to maximize the silane loading of the glass substrate. The reactive functionality deposited on the silica particles is the same as the functionality previously discussed for particulate polymer supports.

One having ordinary skill in the art will select any silanizing agent which forms a silicon ether bond with the reactive silicon on the surface of the siliceous support and which will react with the reactive groups on the activated buckminsterfullerenes. For example, one having ordinary skill in the art may use silanes of the formula:

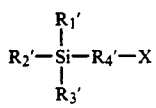

or

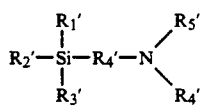

wherein, $R'_1$, $R'_2$ and $R'_3$ each may be halogen, hydroxy, alkoxy, aryloxy, or an alkyl or aryl ester;

$R'_4$ may be a hydrocarbon chain containing one to eight carbon units or a single aryl ring;

$R'_5$ and $R'_6$ each may be hydrogen or a hydrocarbon chain containing one to four carbon units; and, X is halogen as previously defined.

In a preferred embodiment of this invention, $R'_4$ is a hydrocarbon chain containing one to four carbon units and X is chloro.

Representative compounds of the above generic formulas include:
$Cl_3Si(CH_2)_3Cl$
$(HO)_3Si\ C_6H_4CH_2Cl$
$Cl_3SiCH_2Cl$
$(CH_3COO)_3Si(CH_2)_2Cl$
$(CH_3O)_3Si(CH_2)_3N(H)CH_3$
$(CH_3O)_3Si(CH_2)_3N(H)(CH_2)_2NH_2$ The siliceous support is treated with an aqueous solution of the silanizing agent at elevated temperature. The treated support is filtered, washed and dried overnight at 100° C. to polymerize the silicone layer.

Typical siliceous supports containing reactive functionality are regarded as the precursor structures prior to reaction with quaternizing agents as shown in U.S. Pat. No. 4,118,316, to Talley et al., which is herein incorporated by reference.

The siliceous supports can be pretreated to contain hydroxyl functionality on their surfaces, and optionally reacted with the silanizing agent. The reaction of silanizing agents with pendant hydroxyl groups on the silica particle produces oxy-silano substituents on the silica particles. In the alternative, hydroxylated silica particles can be directly reacted with activated buckminsterfullerenes. Silica particles for use in the present invention include talc, kaolinite, pyrophyllite, sepertine, smectite, montmorillonite, mica, vermiculite, silica powder, porous glass, kieselguhr or diatomaceous earth.

The novel chemically bound lattice structures according to this invention can be prepared by the direct reaction of the functional groups on the support particles namely, the polymer particles or siliceous particles, with reactive groups on the activated buckminsterfullerenes. It is preferable, however, to employ spacers or spacer units to reactively link the functional groups on the particulate supports and the activated buckminsterfullerene. The spacer units can be provided by any multi-functional organic compound, i.e. a spacer compound having at least two functional groups, one group being reactive with the functional groups on the support particles and a second group being reactive with the functional groups on the activated buckminsterfullerenes. Spacer compounds are represented by:

$$X_1-Z-X_2$$

wherein Z represents a spacing unit between the support particle and the buckminsterfullerene with the size and type of spacer being comparatively uncritical. $X_1$ represents a first functional group that is reactive with a functional group on the support particle and $X_2$ represents a second functional group that is reactive with a functional group on the activated buckminsterfullerene. The $X_1$ and $X_2$ groups on the spacer units may be identical. Preferably the spacer compound is first stoichiometrically prereacted either with the reactive group on the activated buckminsterfullerene or the reactive group on the particulate supports.

Typical examples of spacers include but are not limited to: $(X_1)-(CH_2)_n-(X_2)$ or $(X_1)-(C_6H_4)-[CR'_1R'_2-(C_6H_4)]_{0-1}-X_2$, wherein $R'_1$ and $R'_2$ have been previously defined; n=2 to 20, preferably 6 to 18; $X_1$ and $X_2$ are the same or different and can be any functionally reactive groups as previously identified as a complementary reactive group, preferably $NH_2$, OH, COOH, oxirano, Li or halo.

Most preferable spacer compounds are represented by the formula:

$$X_1(CH_2)_{6-18}X_2$$

wherein $X_1$ and $X_2$ are independently $NH_2$, OH, Li or COOH.

Anionic initiators such as alkyl lithium compounds, preferably n-butyllithium and tert-butyllithium, may be reacted with halo functional groups on a support particle, an activated buckminsterfullerene or a spacing unit to provide a reactive lithium end group in place of the halo group. Subsequent coupling of the spacing unit, support particle or buckminsterfullerene to corresponding particles or buckminsterfullerenes occurs via removal of the lithium end group and the halo group on a support particle support or buckminsterfullerene.

The buckminsterfullerene bound to support particles as prepared in the present invention display utility as stationary phases and packing media for chromatographic columns. These chromatographic materials display particular utility as an efficient, one-step fractionation and enrichment means for the separation and chromatographic analysis of mixtures containing PNA hydrocarbons, PCB isomers, chlorinated naphthalene, and similar low-tolerance pesticidal and industrial chemicals which exist as pollutants in the environment, as well as for separation of fullerene mixtures. Such mixtures of hazardous compounds are often encountered in laboratory specimens in combination with natural materials including plant pigments and tissue, and biological fluids and tissue, together with organic solvents, laboratory reagents and herbicides and insecticides which are not toxic to higher life forms. Heretofore, two or more chromatographic columns had been required to fractionate and isolate the components of such complex mixtures. Specific applications of this invention are in the separation of planar polychlorinated biphenyls (PCBS) from mixtures which also include at least one non-planar PCB and other polynuclear aromatic hydrocarbons, and in the enhanced separation of fullerenes $C_{60}$, $C_{70}$ and higher order fullerenes.

In the following examples illustrating the invention, all parts and percentages are parts by weight unless stated otherwise.

EXAMPLE 1

Synthesis of $C_{60}HO(CH_2)_8HN$-Polystyrene Chromatography Resin

This example details the reaction schemes and procedures employed in synthesizing a preferred chromatographic material of the present invention. Various analytical techniques, including UV, FAB-MS, $^{13}C$-NMR, and Magic Angle Spinning $^{13}C$-NMR were used for structure identification.

1(a) Hydroboration-Bromination of $C_{60/70}$

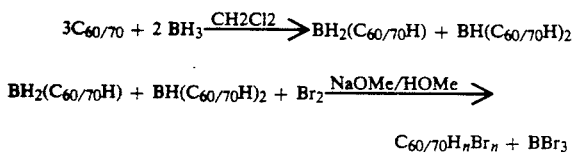

wherein $C_{60/70}$ denotes either $C_{60}$, $C_{70}$ or a mixture thereof.

While other reactions such as Birch reduction may be employed to add bromine to a $C_{60}$ or $C_{70}$ molecule, the hydroboration-bromination reaction set provides better control over the number of double bonds opened, and thereby the number of bromine atoms that react with each $C_{60/70}$ molecule. Conjugated double bonds of $C_{60/70}$ molecules increase their resonance energy, and are responsible for their molecular stability and strength. Hence, addition of bromine to the fullerene structure should be kept to a minimum number in order to preserve these desirable properties.

Synthesis Procedure

A suspension of 80 mg of $C_{60/70}$ obtained from MER Co. (Tucson, Ariz.) in 120 ml of dichloromethane $(CH_2Cl_2)$ was poured into a 250 ml three-neck flask equipped with condenser and magnetic stirrer. At room temperature and under inert argon atmosphere, 0.5 ml of a solution of boron hydride $(BH_3)$ in tetrahydrofuran was then added to the flask. After 7 hours of reaction, 1.5 ml of methanol $(CH_3OH)$ was added to react excess $BH_3$.

After the reaction flask was cooled to 7° C., 0.25 ml of liquid bromine and 0.4 g of sodium methoxide $(NaOCH_3)$ in 15 ml of methanol, were then successively added, and the reaction mixture was stirred for 15 hours at room temperature. The product mixture was filtered, and the solvent was evaporated under vacuum. The residue was dissolved in 120 ml of $CH_2Cl_2$. A white precipitate was separated by centrifugation. The clear, red solution was washed with $2 \times 60$ ml of water, and $2 \times 70$ ml of saturated potassium carbonate $(K_2CO_3)$. The solution was then washed with 80 ml of water. The organic layer was dried with anhydrous $K_2CO_3$. Evaporation under vacuum yielded a violet-red solid product.

Figure 2A:
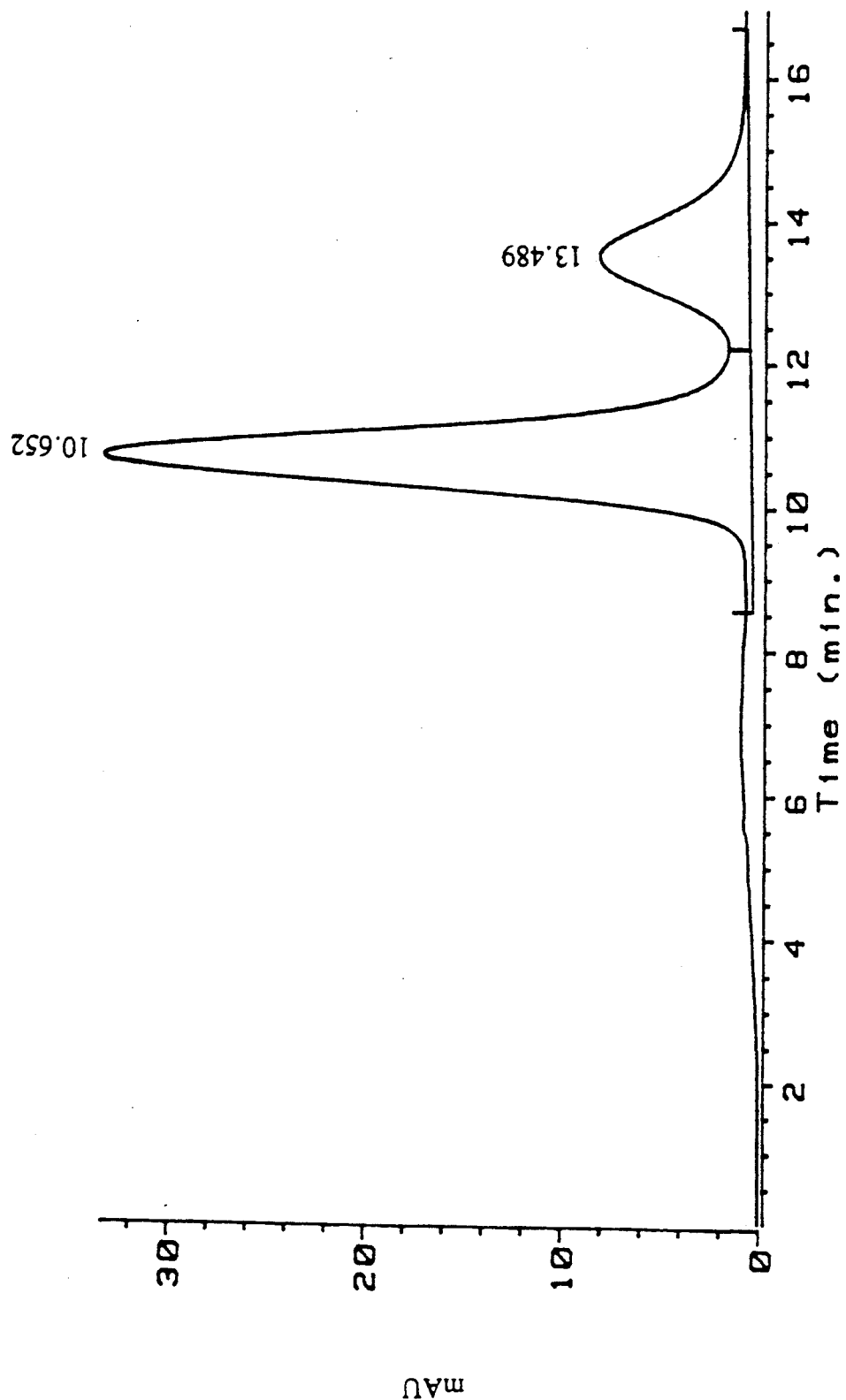
Figure 2B:
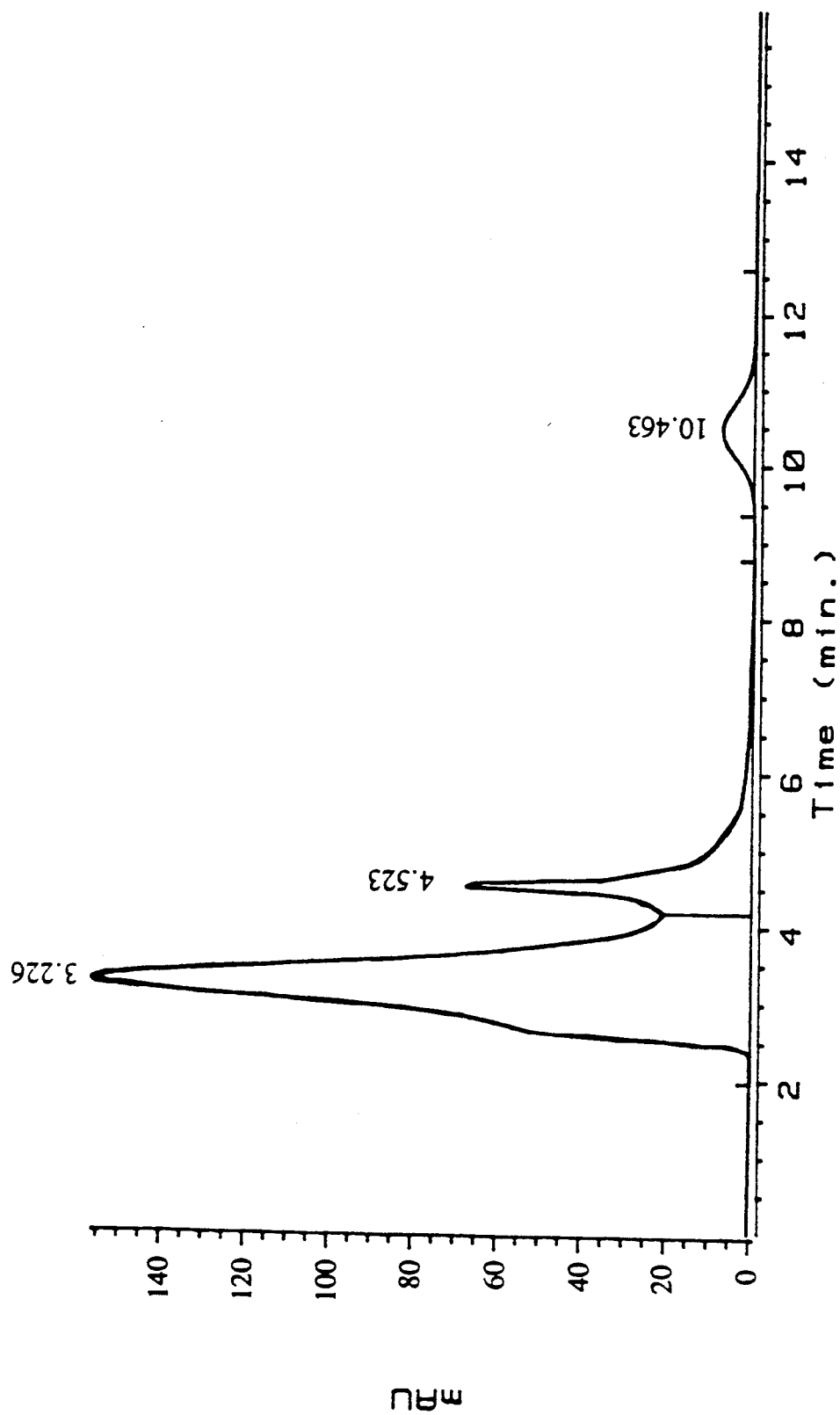

FIGS. 2A and 2B show the high performance liquid chromatography (HPLC) UV chromatogram of a mixture of $C_{60}$ and $C_{70}$ and of the product solution respectively obtained by elution with methylene chloride through a 50 mm long $\times$ 7.8 mm I.D. guard column in series with a 300 mm long $\times$ 7.8 mm I.D. separation column. These Envirosep-ABC columns contain 10 μm O.D. PSDVB beads. The separation of fullerenes and their substituted derivatives using Envirosep-ABC columns is described in detail in a co-pending U.S. applications by Stalling et al.

The reaction products eluting at 3.2 minutes (fraction 2) were collected for structure characterization. Minor peaks at 2.5 min and 4.5 min were also separately collected. The peak eluting at 10.5 min corresponds to unreacted $C_{60}$. Since induced pi-pi interaction of the fullerenes with the PSDVB resin is chiefly responsible for the adsorptive chromatography behavior exhibited by this separation, the lower retention times of all reaction products indicates partial loss of aromaticity by the fullerenes.

Figure 2C:
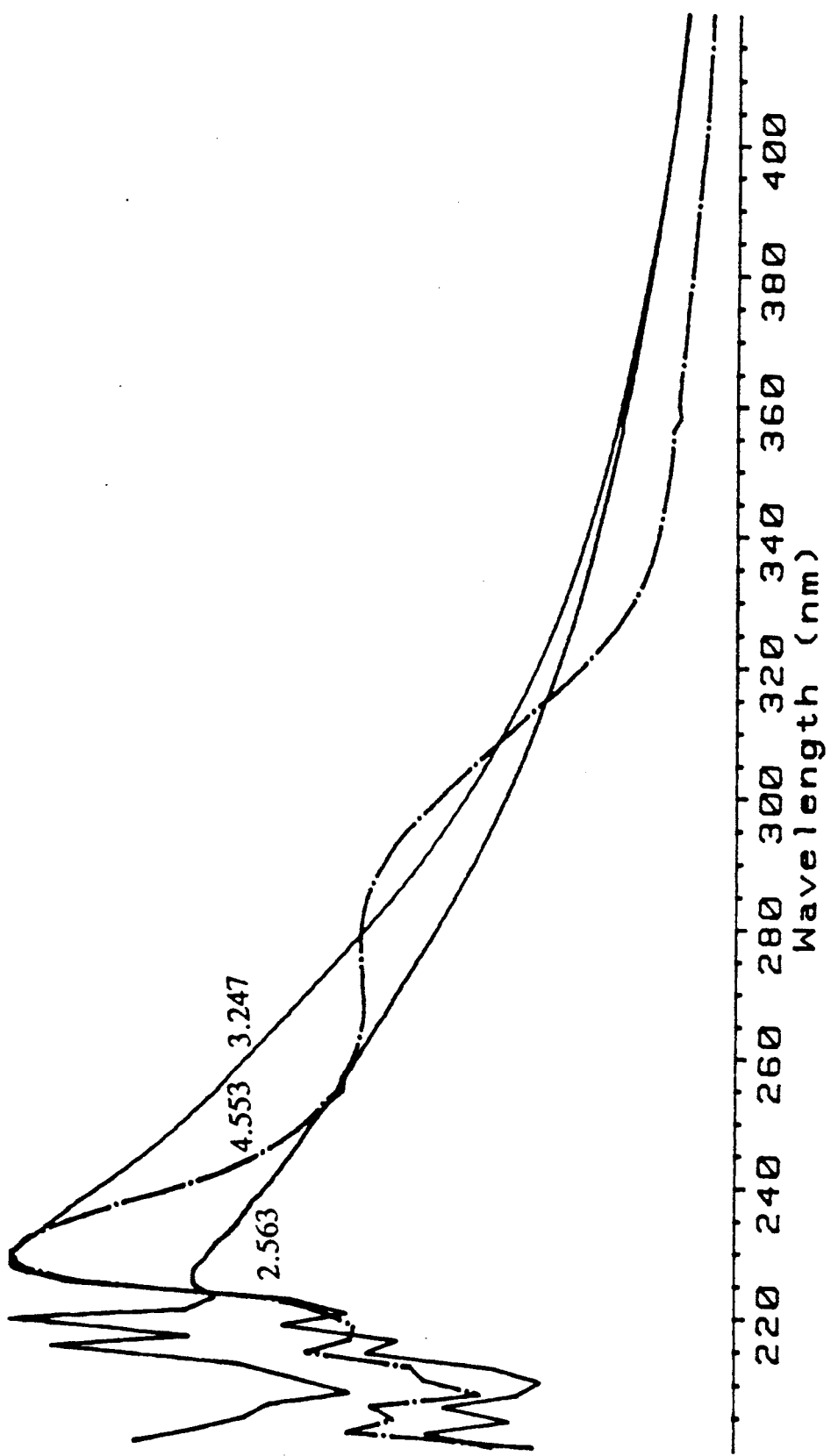

FIG. 2c displays the UV spectra of all three fractions. All three fractions absorbed strongly in the 220–240 nm range, indicating their similarity. The 4.5 min fraction also absorbed strongly in the 280–300 nm range. The 4.5 min fraction absorbed in ranges close to those of $C_{60}$ (240–280 nm and 310–350 nm), and thus indicates that it has preserved a substantial fraction of its aromaticity. Loss of aromaticity has the overall effect of shifting maximum absorption to lower wavelengths.

Structure Characterization of Reaction Products of Example 1(a)

Negative Ion FAB-MS Characterization

Figure 3:
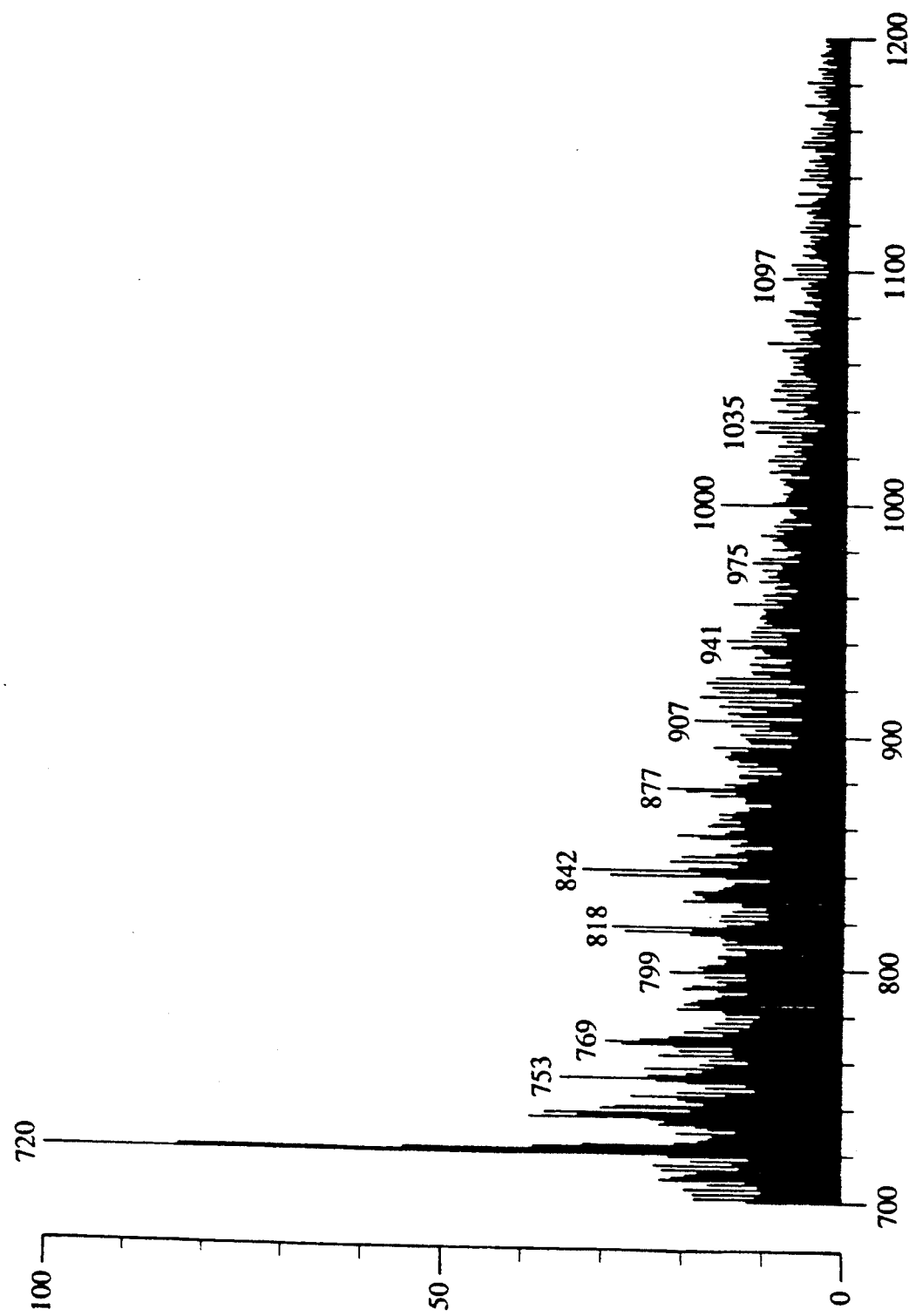

Negative Ion Fast Atom Bombardment-Mass Spectroscopy fragmentation patterns of the reaction products in fraction 2 are shown on FIG. 3. Mass to charge ratios (m/z) correspond to the following entities:

| m/z | Ion |
|-----|-----|
| 720 | $C_{60}H$ (from $C_{60}HBr$) |
| 799 | $C_{60}HBr$ |
| 818 | $C_{60}HBr$—$HOH$ |
| 842 | $C_{70}H_2+$ (from $C_{70}H_2Br_2$) |
| 877 | $C_{60}Br_2$ |
| 1000 | $C_{70}H_2Br_2$ |
| 1035 | $C_{60}Br_4$ |

Other ions were not identified, but it is ascertained that the reaction product bears aromaticity, and addition of 1 to 4 bromine atoms per reacted fullerene molecule has taken place.

$^{13}C$-Nuclear Magnetic Resonance

Figure 4B:
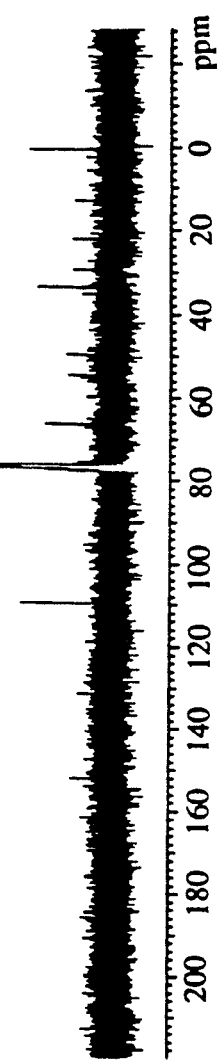

FIG. 4A shows the NMR spectrum of a mixture of $C_{60}$ and $C_{70}$. $C_{60}$ has only one chemical shift at 143.1 ppm, while $C_{70}$ has 5 chemical shifts at 130.1, 145.4, 147.4, 148.1, and 150.7 (J. Chem. Phys., 94, p. 8630, 1990). Chemical shifts of $C_{70}$ in FIG. 4A appear weaker than those of $C_{60}$ due to the low concentration of $C_{70}$ in the mixture (less than 15%). FIG. 4B shows the NMR spectrum of fraction 2 solution. Several regions of strong chemical shifts, between 68 and 12 are observed. No major chemical shift was detected at 143 ppm, indicating that no $C_{60}$ was present in this fraction, although the reacted $C_{60/70}$ still conserves some aromaticity as indicated by peaks from 154 ppm to 110 ppm. Displacement in the chemical shift to high field as compared to pure $C_{60}$ is also an indication of the loss in aromaticity. The multitude of chemical shifts is an indication of the degree to which carbon-carbon conjugated bonds in the fullerenes were opened by addition of reactants.

1(b) Adsorption of 3,3',4,4'-Tetrachloro-biphonyl in Cyclopentane

In order to further ascertain that the reaction product in fraction 2 bears aromaticity, the extent of adsorption of a PCB by the reaction products was determined as follows: First, 2.5 μg of 3,3',4,4' PCB were dissolved in 1 ml of cyclopentane. Injection 50 μl of this solution yielded a PCB HPLC UV peak area of 187 units. Next, 30 mg of the solid reaction product in fraction 2 was added to 1 ml of cyclopentane containing 2.5 μg of the PCB. The solution was shaken for ½ hour, and then allowed to settle. The PCB HPLC UV peak area of the supernatant solution was 155. This indicates adsorption of 0.014 μg of PCB per mg of reaction product.

Note that because cyclopentane is non-aromatic, it is not expected to solubilize any measurable amounts of the reaction product. Thus, if the reaction product were non-aromatic, it would not have adsorbed any significant amount of the aromatic PCB. Thus, this result is a further evidence that the reaction product still bears aromaticity.

1(c) Synthesis of $C_{60/70}H_n[O(CH_2)_8Br]_n$

An alkoxy group was attached to the $C_{60/70}$ molecule to act as spacer between $C_{60/70}$ and a polystyrene or other resin or silica support. This spacer was long enough to significantly reduce interference of stereo and chemical hindrances of the support on the chromatographic properties of $C_{60/70}$. The following reaction schemes were employed to produce such intermediate product:

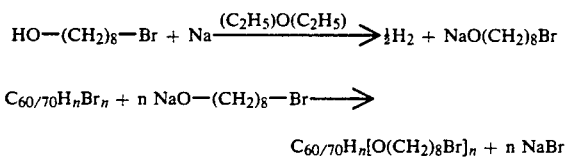

$$HO-(CH_2)_8-Br + Na \xrightarrow{(C_2H_5)O(C_2H_5)} \tfrac{1}{2}H_2 + NaO(CH_2)_8Br$$

$$C_{60/70}H_nBr_n + n\ NaO-(CH_2)_8-Br \longrightarrow$$

$$C_{60/70}H_n[O(CH_2)_8Br]_n + n\ NaBr$$

Synthesis Procedure

A charge of 0.0506 g of metallic sodium was added, at room temperature and under inert argon atmosphere, to 80 ml of anhydrous ethyl ether ($(C_2H_5)O(C_2H_5)$) contained in a 250 ml three-neck flask equipped with condenser and magnetic stirrer. A charge of 0.4 ml of 8-bromo-1-octanol ($HO-(CH_2)_8-Br$) was then added to the mixture and the reaction mixture was refluxed gently for about 4 hours until all sodium was reacted. Thereinafter 0.175 g of $C_{60/70}H_nBr_n$, as prepared in Example 1(a), in 30 ml of anhydrous ethyl ether, was added to the mixture.

Following reaction under reflux for about 23 hours, the mixture was cooled to room temperature and the solvent was evaporated under vacuum. To the resultant product was added 140 ml of dichloromethane and 80 ml of water. The organic layer was saved and the water layer was further extracted with 70 ml of dichloromethane. The combined organic layer was washed with 100 ml of water and 100 ml of saturated NaCl, then dried over anhydrous $K_2CO_3$. Solvent evaporation under vacuum yielded 0.154 g of a violet-red liquid.

Figure 5:
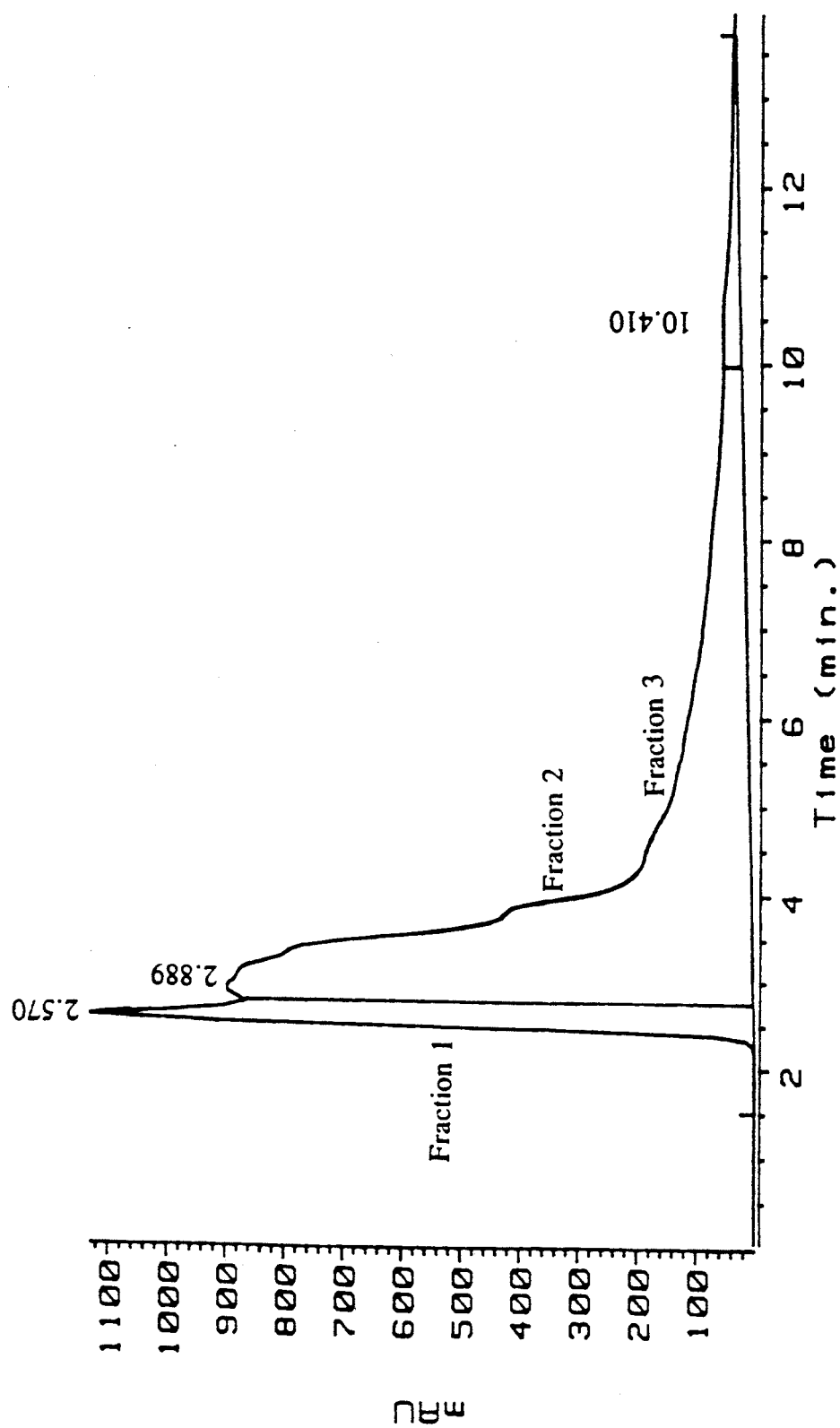
Figure 6:
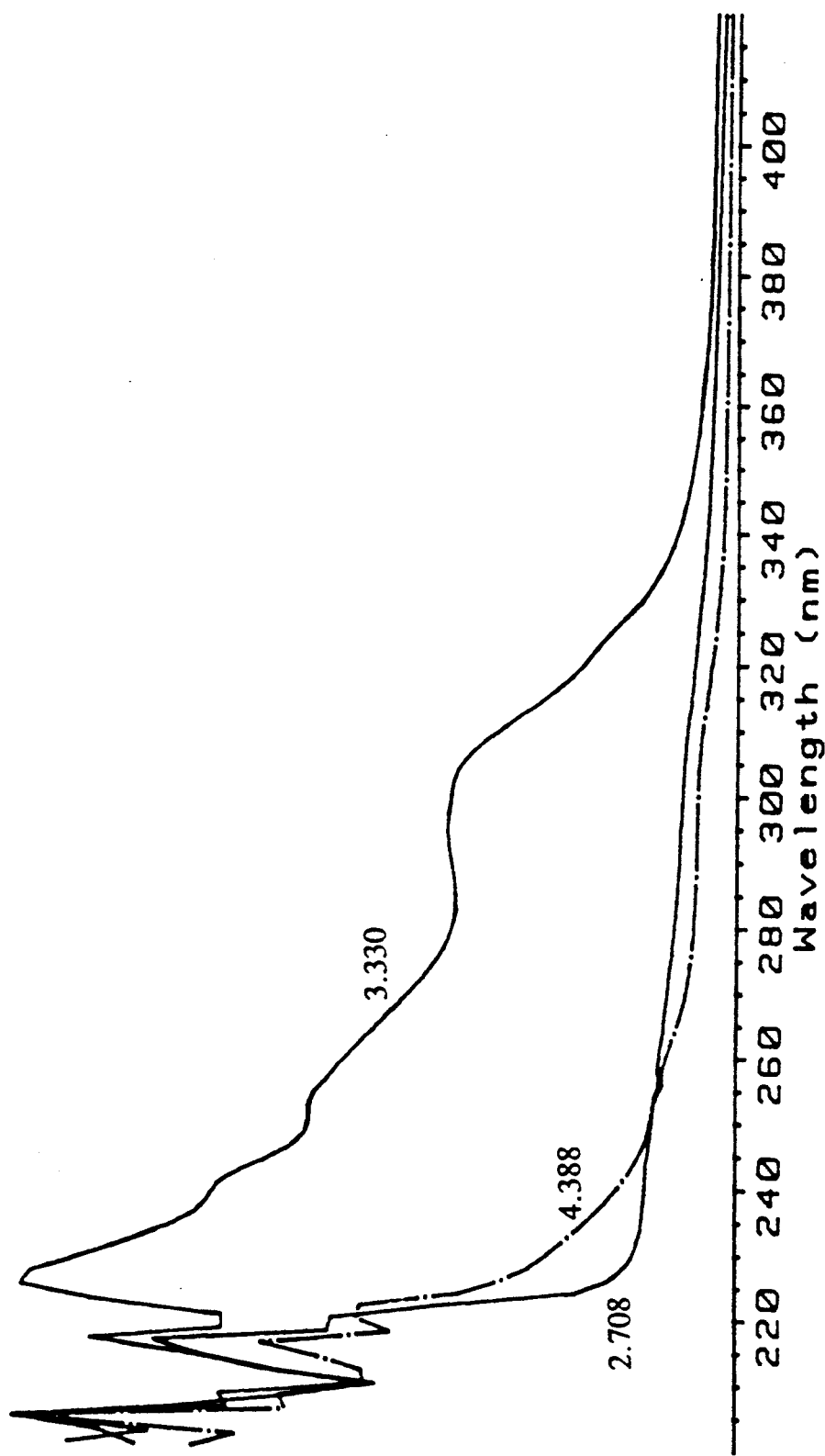

FIG. 5 displays the HPLC UV chromatogram of this product mixture in toluene solution obtained by elution through a 50 mm long×7.8 mm I.D. guard column in series with a 300 mm long×7.8 mm I.D. separation column. FIG. 6 displays the UV spectrum of all 3 fractions. Only the 3.33 peak (fraction 2) shows any major aromaticity. This fraction was collected for structure characterization as follows.

Structure Characterization of Reaction Products

(i) Negative Ion FAB-MS Characterization

Figure 7A:
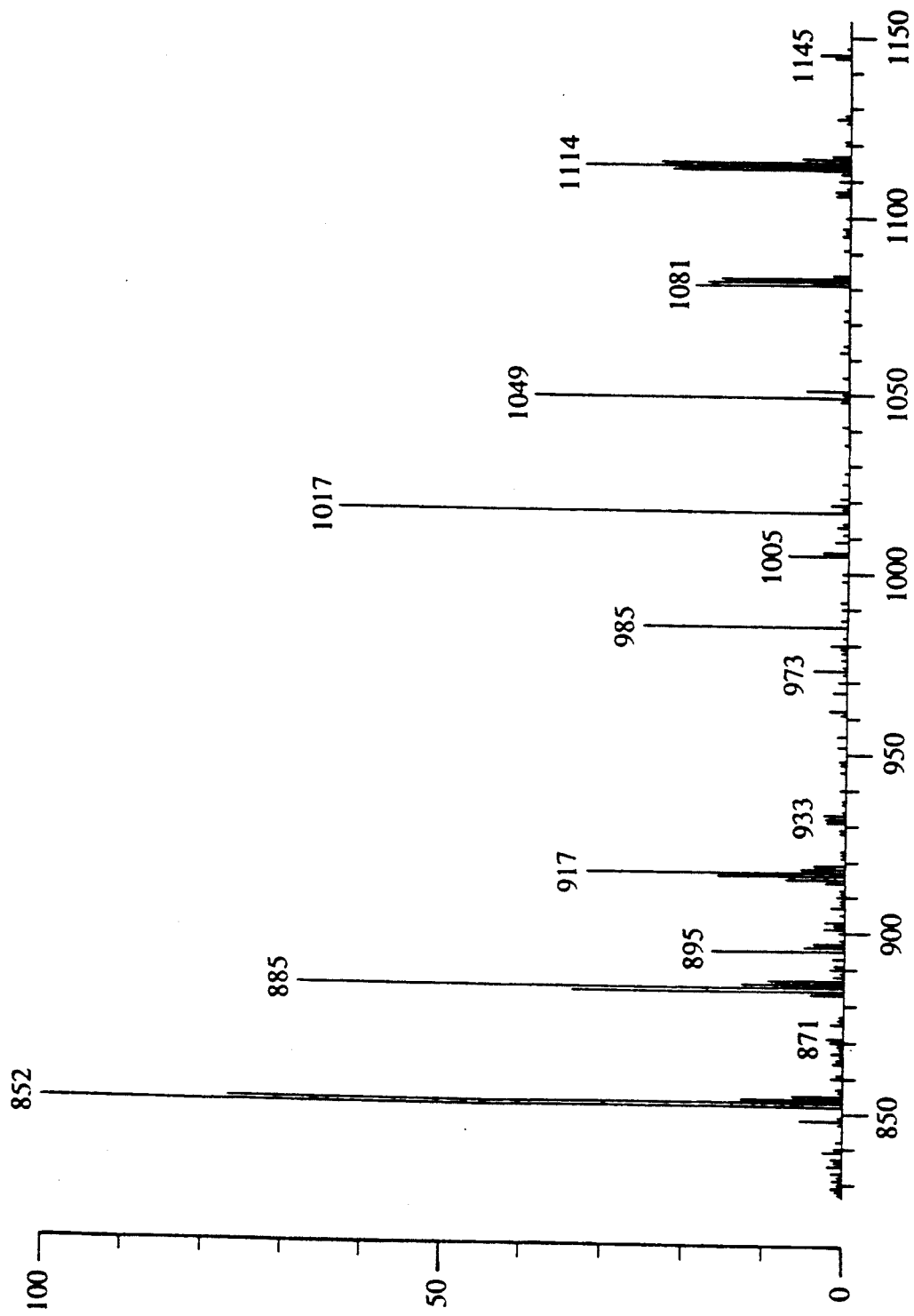

Negative Ion Fast Atom Bombardment-Mass Spectroscopy fragmentation patterns of the reaction products in fraction 2 are shown in FIG. 7A. A mixture of dithioerythritol and dithiothritol was used as magic bullet. Mass to charge ratios (m/z) correspond to the following entities:

| m/z | Ions |
| --- | --- |
| 852 | $C_{60}H_5O(CH_2)_8$ (from $C_{60}H_5O(CH_2)_8Br$) |
| 931 | $C_{60}H_5O(CH_2)_8Br$ |
| 1017 | $C_{60}OH,O(CH_2)_8$ + 153 (magic bullet) |
| 1081 | $C_{60}HO(CH_2)_8Br$ + 153 (magic bullet) |
| 1114 | $C_{70}HOH,(O(CH_2)_8)_2$ |

Other ions were not identified.

(ii) $^{13}$C-Nuclear Magnetic Resonance

Figure 7B:
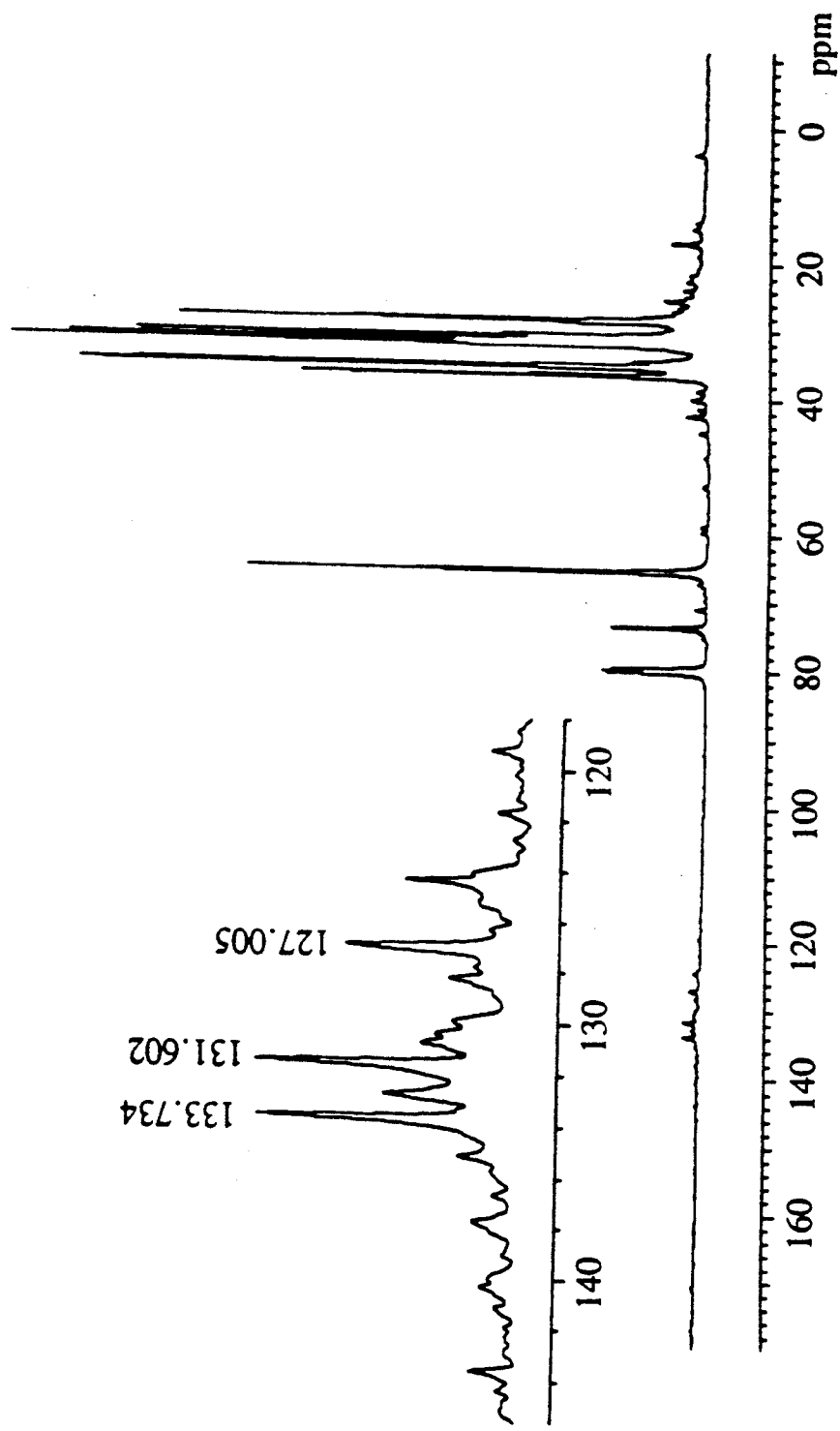

NMR spectrum of fraction 2 solution in the 0–200 ppm range show chemical shifts for aromatic and conjugated double bonds at 131, 129, and 121 (FIG. 7B). Chemical shifts at 68, 57, 42, 39, 37, 32, 30, 23, 21, 14, and 11 ppm are from single bond carbons of $C_{60}$ and $C_{70}$, while a strong shift at 71 ppm is from $O-C_{60}$. Chemical shifts at 69, 63, and 34 ppm are from $C-C_{60}$, $O-CH_2$, and $Br-CH_2$ respectively. Six chemical shifts from 33–25 ppm are from 6 $CH_2$ carbons.

(iii) Adsorption of 3,3'4,4'-Tetrachlorobiphenyl in Cyclopentane

A sample of 2.5 μg of 3,3',4,4' PCB was dissolved in 1 ml of cyclopentane. The PCB eluted 13.1 min, and its peak area was 204 units. Next, 70 mg of the reaction product in fraction 2 was added to 1 ml of cyclopentane containing 2.5 μg of the PCB. The solution was shaken for ½ hour, and allowed to settle. Peak area of the PCB was negligible. This indicates that the reaction product is a good adsorbent for aromatic compounds, and it is thus inferred that this reaction product bears aromaticity.

1(d) Synthesis of Polystyrene-NH₂

Polystyrene $NH_2$ was used as intermediate in the production of the polystyrene copolymer linked to $C_{60/70}$. First, polyacrylic acid, a stabilizer for polystyrene, was synthesized.

1(d)(i) Synthesis of Polyacrylic Acid

A charge of 9.5 ml of acrylic acid, 67.7 ml (70 g) of dioxane, and 0.02 g of 2,2'-azobis(2-methylpropionitrile) (AIBN) was poured into a 250 ml three-neck flask equipped with condenser and stirrer. After stirring for 7 hours at 63° C., the colorless liquid was transferred into a beaker and 200 ml of petroleum ether was then added. The solution was evaporated under vacuum to yield 11.89 g of a white solid residue of polyacrylic acid.

1(d)(ii) Synthesis of Uniform Polystyrene Particles by Dispersion Polymerization Polystyrene beads of average size of 1.9 μm are synthesized by reaction of polyacrylic acid with styrene and AIBN as follows:

Polyacrylic Acid + Styrene + AIBN → Polystyrene

First, 1 g of polyacrylic acid was mixed with 20 ml of water and 50 ml of ethanol in a 250 ml three-neck flask equipped with condenser and stirrer. The solution was then stirred for about 5 minutes to dissolve the polyacrylic acid. A solution of 0.14 g of AIBN in 10 ml of styrene was then added to the mixture. The reaction mixture was then stirred for 24 hours at 70° C. in an argon atmosphere. A white latex milk (85 ml) containing 1.9 μm O.D. particles was obtained. This synthesis is depicted in FIG. 1, reaction (1).

In order to reduce pressure drops along a chromatography packed column, the packing particle size should be larger than 2 μm, preferably larger than 5 μm. Surface modification of the polystyrene bead to increase its size to more than 2 μm, and to attach to it an amino group was performed according to the following reaction scheme:

1(d) (iii) Synthesis of Uniform, Surface Modified Polystyrene-NH$_2$Particles by Seeded Polymerization

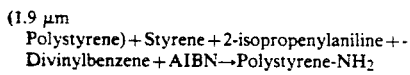

(1.9 μm Polystyrene) + Styrene + 2-isopropenylaniline + Divinylbenzene + AIBN → Polystyrene-NH$_2$ First, 55 mg of AIBN in 4 ml of styrene, 1.0 ml of divinyl benzene and 0.3 ml of 2-isopropenylaniline was added to the polystyrene bead product of the previous reaction (85 ml) in an argon atmosphere. The mixture was then stirred for 48 hours at 3° C. Reaction temperature was then increased to 70° C. to initiate copolymerization, and maintained at this level for 24 hours. Lyophilizing (i.e. freeze-drying) of the mixture yielded a yellowish solid. This synthesis is depicted in FIG. 1A, reaction (2).

Electron microscopy revealed that the average diameter of the surface modified polystyrene particles is 2.3 μm.

(i) Structure Characterization of Reaction Products

Aromatic Amino Function Group Test: Positive. The reaction product turns red with ə-naphthol test, indicating the presence of —NH$_2$ function group.

Figure 8:
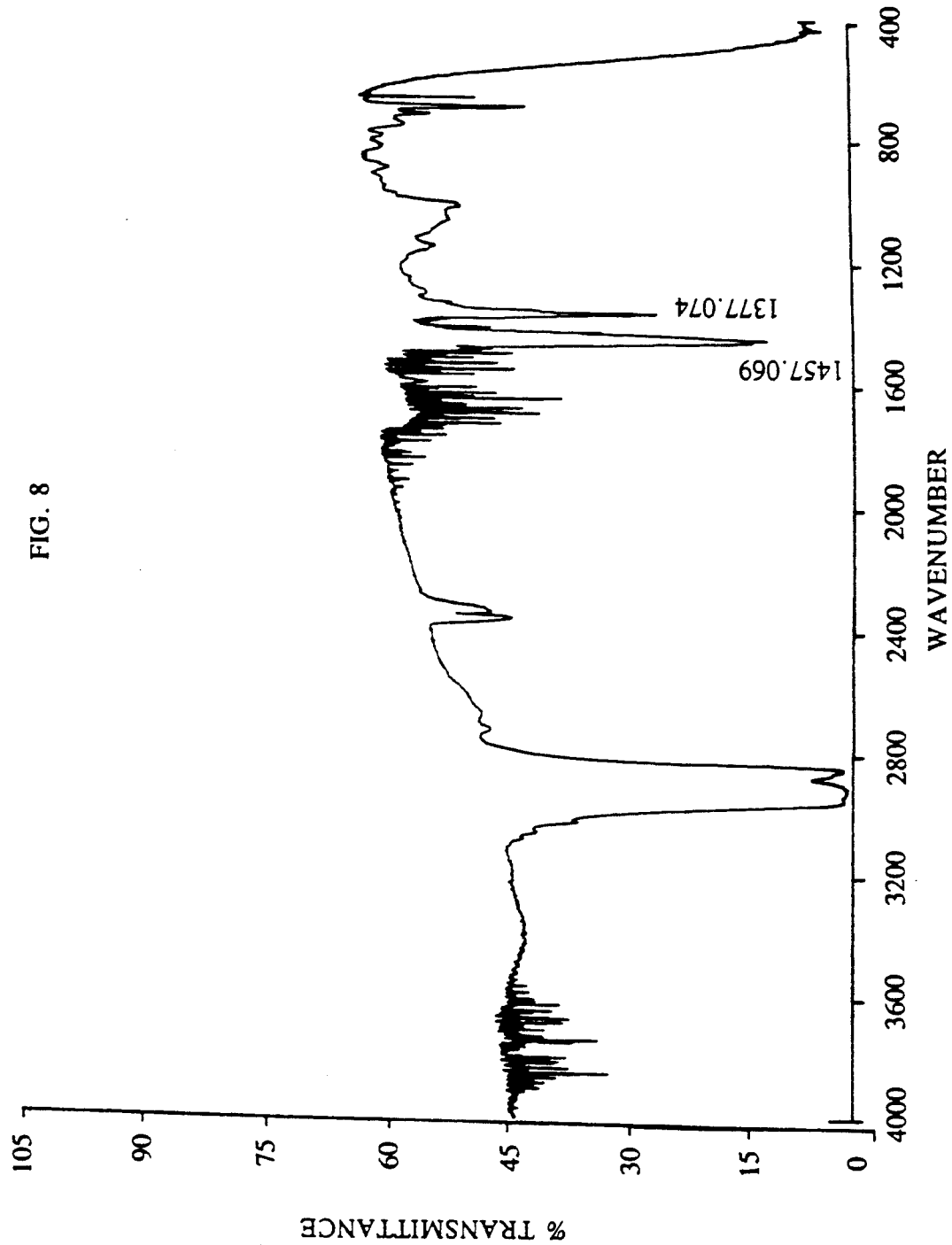

Fourier Transform-Infra Red: The FT-IR of the reaction product is shown in FIG. 8. Absorption bands at 3500 to 3200 and 1650 cm$^{-1}$ are for —NH$_2$ function group. Absorption bands at 1630, 1457, 1377, and 1100–900 cm$^{-1}$ are for —C$_2$H$_5$, (—CH$_2$ and —CH$_3$), —CH$_3$, and (—C$_6$H$_5$ and —C$_6$H$_4$) respectively.

Figure 9A:
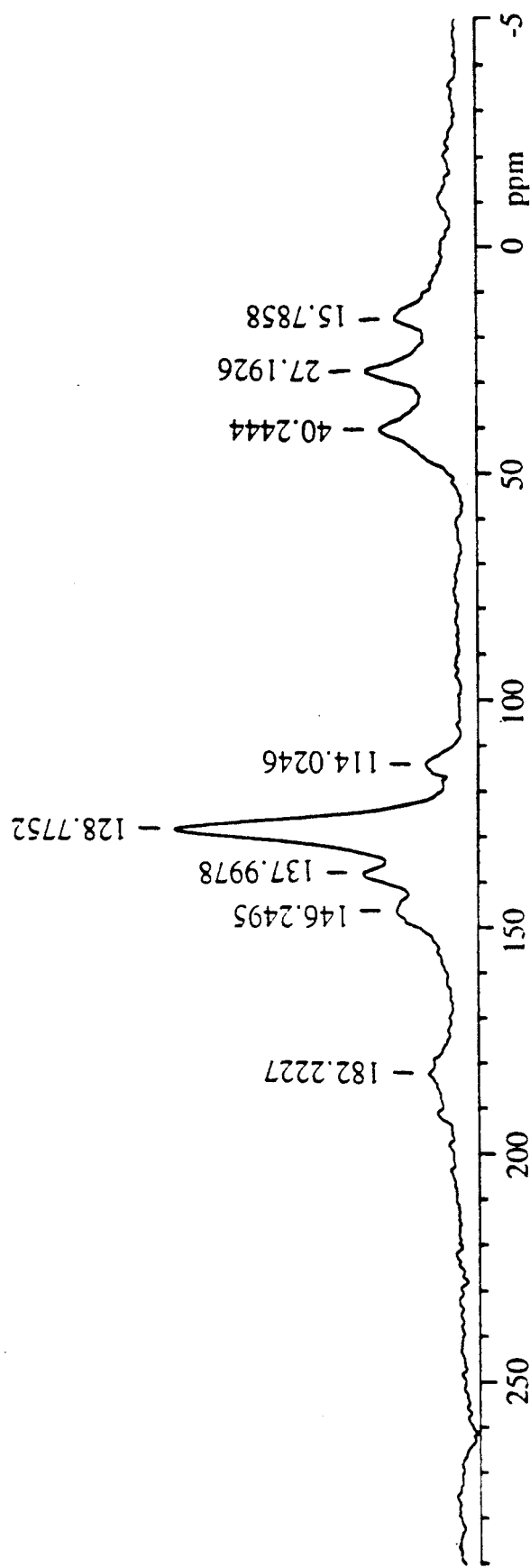
Figure 9B:
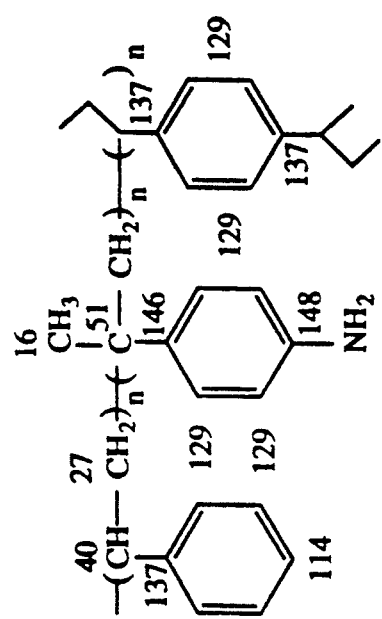

Magic Angle Spinning $^{13}$C-NMR: FIG. 9A shows the spectrum of the reaction product obtained by magic angle spinning 13C NMR, and FIG. 9B its inferred molecular structure. Chemical Shifts for all the carbons in polystyrene-NH$_2$ were observed.

PCB Adsorption Test: The number of area units (371) of the PCB peak in the solution in contact with the reaction product, i.e. adsorbent, (5 μg of PCB in 1 ml of cyclopentane + 23 mg of Polystyrene-NH$_2$ particles) is only 2.3% lower than the reference mixture (no absorbent), indicating that the polystyrene adsorbs only a negligible amount of PCB.

1(e) Synthesis of C$_{60/70}$HO(CH$_2$)$_8$—NH-Polystyrene

This step in this Example describes the last step in the preparation of the C$_{60}$/C$_{70}$ linked polystyrene chromatography material by the following reaction:

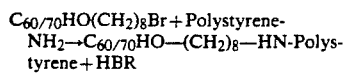

C$_{60/70}$HO(CH$_2$)$_8$Br + Polystyrene-NH$_2$ → C$_{60/70}$HO—(CH$_2$)$_8$—HN-Polystyrene + HBR First, a solution of 20 mg of polystyrene-NH$_2$ in 20 ml of deionized water was mixed with 5 ml of ethylene glycol dimethylether (EGDE). Following addition of a pH 10 buffer to adjust the pH to 5, the mixture was homogenized in an ultrasonic bath for 2–3 min. Five (5) ml of a solution of 250 mg of C$_{60/70}$H[O(CH$_2$)$_8$Br]/mL of EGDE is then slowly added to the mixture. The pH of the reaction mixture was then 8.5. The mixture was constantly stirred. Reaction for 94 hours at 32° C. caused the pH to decrease to 6.5. A pH 10 buffer was then added to bring the pH of the reaction mixture to 9, and the reaction was then allowed to proceed for 24 hours. The product was then washed with toluene and a yellowish solid having the following structural characterization was obtained.

Aromatic Amino Function Group Test: No red color, indicating that all the polystyrene-NH$_2$ was reacted.

Figure 10A:
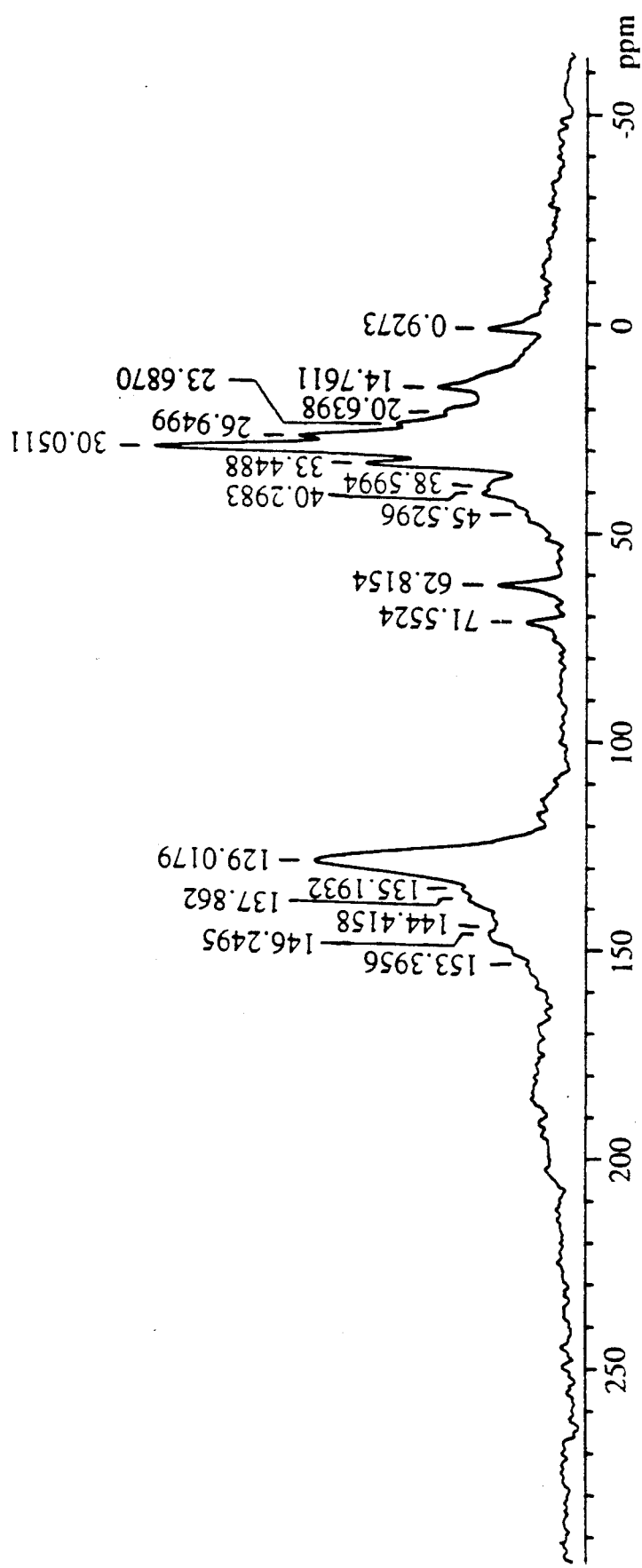
Figure 10B:
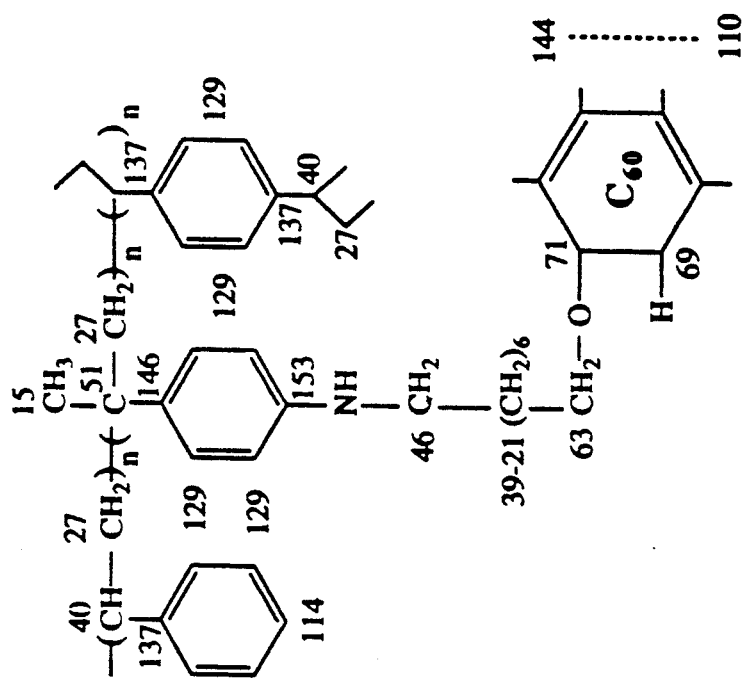

Magic Angle Spinning $^{13}$C-NMR: FIG. 10A shows the spectrum of the reaction product obtained by magic angle spinning $^{13}$C-NMR, and FIG. 10B its inferred molecular structure. Chemical shifts for all carbons in the product were observed.

Figure 11A:
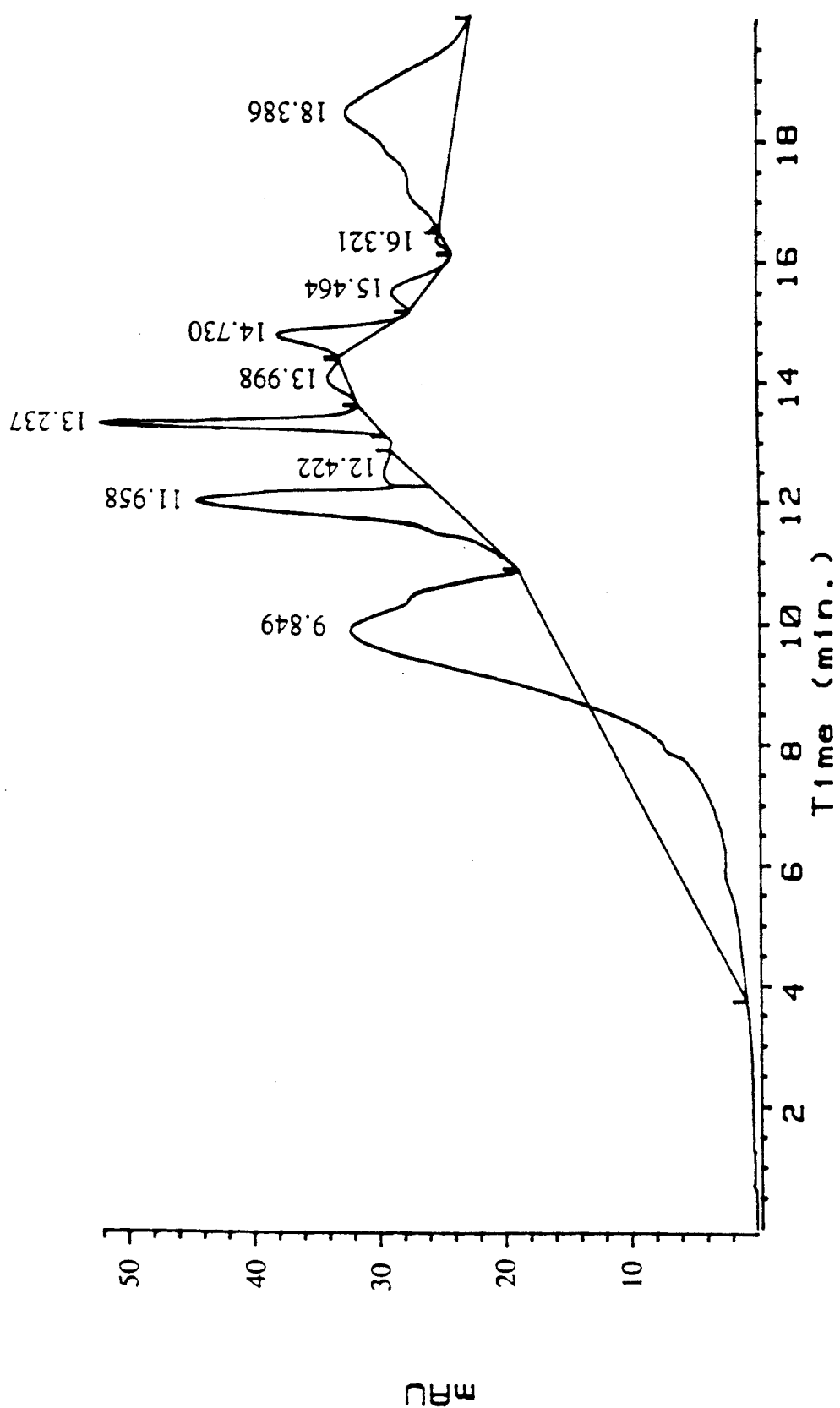
Figure 11B:
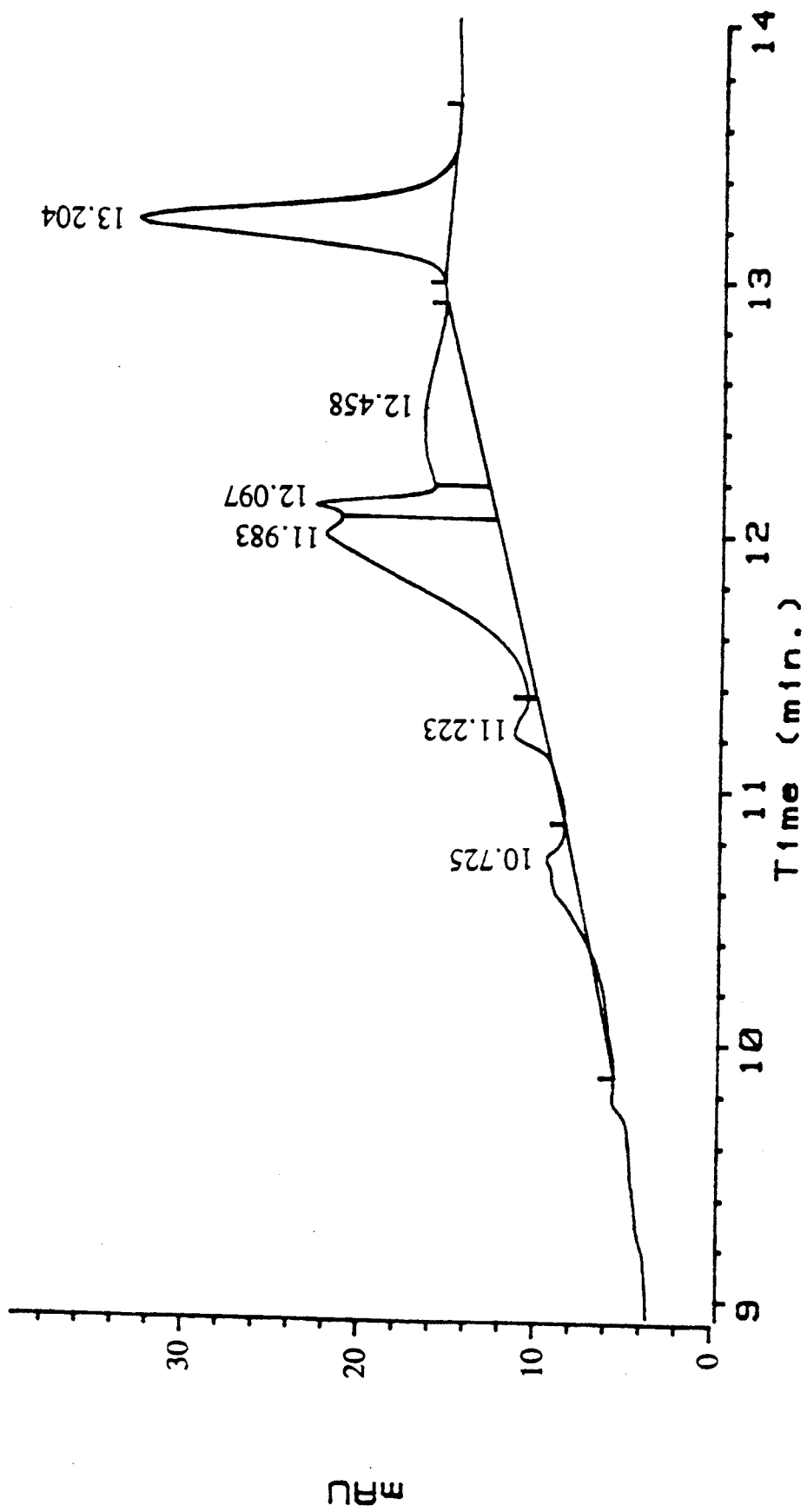

PCB Adsorption Test: Positive. As shown on FIGS. 11A and 11B, the number of area units (171) of the PCB peak in the solution in contact with the reaction product, i.e. adsorbent, (2.5 μg of PCB in 1 ml of cyclopentane + 50 mg of reaction product particles) was 20% lower than the reference mixture, i.e. no adsorbent, (214). The reaction product thus displayed strong adsorption of the aromatic PCB thereby confirming its aromaticity.

EXAMPLE 2

Synthesis of Resin-CH$_2$—C$_{60/70}$Cl

The Envirosep-ABC column packing (EP), which consists of PSDVB particles, was reacted with C$_{60/70}$ to obtain a chromatographic support. First, EP—CH$_2$Cl is synthesized.

2(a) Synthesis of EP—CH$_2$Cl

EP + (CH$_2$O)$_n$/HCl → EP—CH$_2$Cl

The synthesis procedure consists of first adding 0.96 g of paraformaldehyde (CH$_2$O)$_n$, 2.5 ml of glacial acetic acid, 1.5 ml of phosphoric acid (85%), and 4.5 ml of concentrated hydrochloric acid to a 100 ml, three-neck flask equipped with condenser and stirrer. 0.69 g of EP particles (5 μm, 100 Å) is then added, and the reaction mixture is stirred for 16 hours at 85° C. under argon atmosphere.

After centrifugation of the reaction mixture, the solid product is washed with 2×8 ml of concentrated hydrochloric acid, 3×8 ml of deionized water, 3×8 ml of methanol, and 3×8 ml of tetrahydrofuran (THF). Yield of solid product was 0.46 gram.

2(b) Characterization of Reaction Products

Optical Microscope: Positive. The particle uniform morphology is unchanged.

Copper wire test: Positive. Yields a green color flame for the product (no color is observed for the EP particles).

Silver nitrate test: Positive. No AgCl precipitate formed, indicating that there is no free chlorine in the product, and that it is bonded chlorine that gave the positive result from the copper wire test, and not chlorine ions from HCl.

Titration by 0.1N AgNO$_3$: Using a chloride ion electrode a chloromethyl content of 0.42 meq/g is found.

2(c) Synthesis of EP—CH$_2$C$_{60/70}$Cl

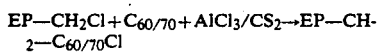

The synthesis procedure consists of first adding into a 100 ml three-neck flask equipped with condenser and stirrer, the following :0.2 g of the product of the previous reaction (EP—CH$_2$Cl) 10 ml of CS$_2$, and 0.035 g of AlCl$_3$. The reaction mixture is then stirred at room temperature for 24 hours.

After filtering, the solid product is successively washed with 6×2 ml of CS$_2$, 6×2 ml of H$_2$O, 6×2 ml of CH$_3$OH, 4×2 toluene, 4×2 ml of CH$_2$Cl$_2$, 3×2 ml of THF, and 4×2 ml of ether. 0.2 g of a yellow-brown product is obtained.

EXAMPLE 3

Synthesis of Resin-C$_{60/70}$H

The Envirosep-ABC column packing (EP) can also be directly linked to C$_{60/70}$ via the following reaction:

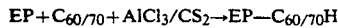

The synthesis procedure consists of first adding 0.2 g of EP, 8 ml of CS$_2$, and 0.09 g of AlCl$_3$ to a 50 ml, three-neck flask equipped with condenser and stirrer. 0.05 g of C$_{60/70}$ dissolved in 15 ml of CS$_2$ is then added under argon atmosphere. The reaction mixture is then stirred at room temperature for 42 hours.

After filtering, the solid product is successively washed with 6×2 ml of CS$_2$, 6×2 ml of H$_2$O, 6×2 ml of CH$_3$OH, 5×2 ml of toluene, 4×2 ml of CH$_2$Cl$_2$, 3×2 ml of THF, and 4×2 ml of ether. 0.205 g of a yellow-brown product is obtained.

Figure 12:
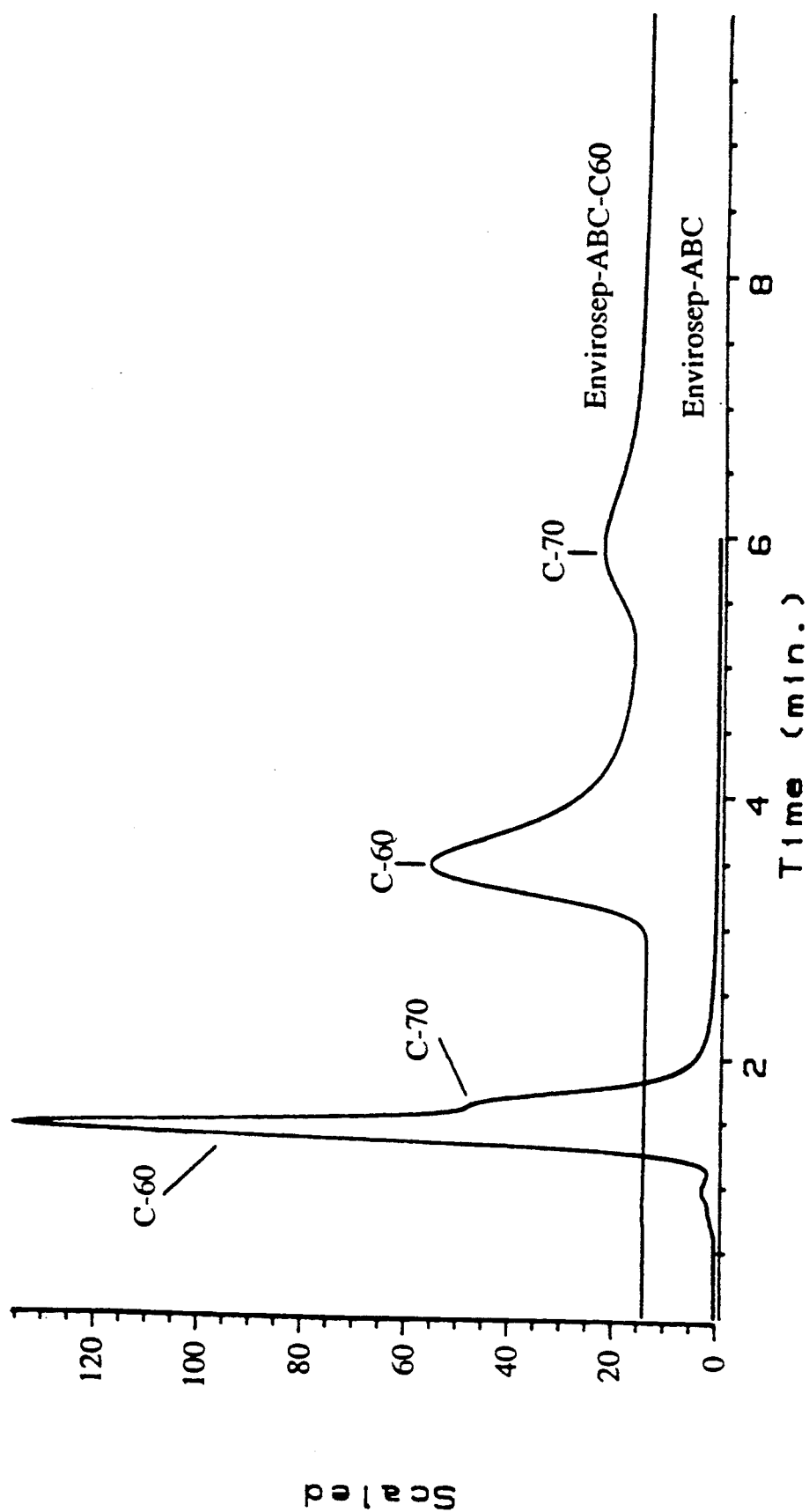
FIGS. 12-14 display properties of products produced in Example 3.
Figure 13:
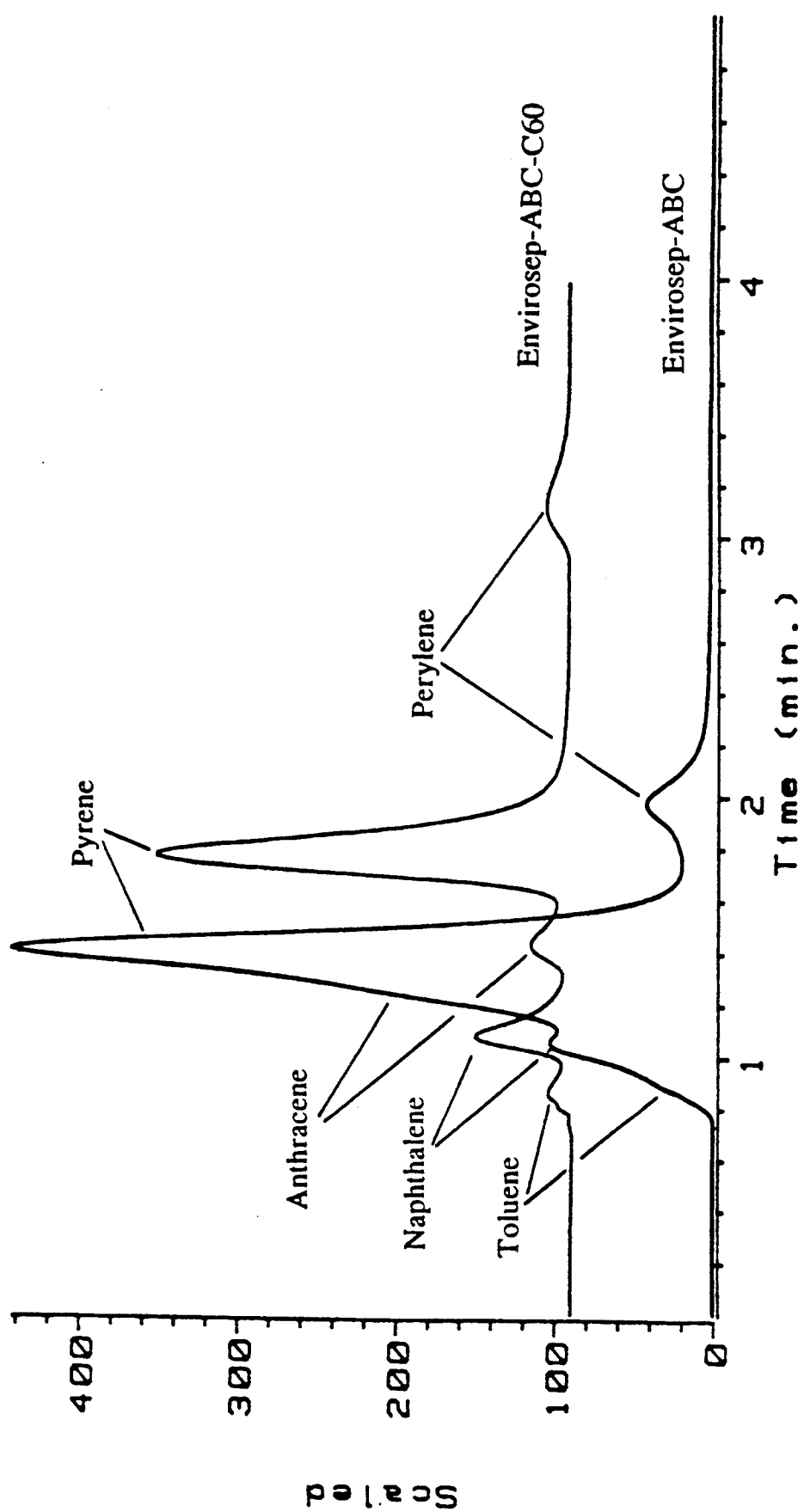
Figure 14:
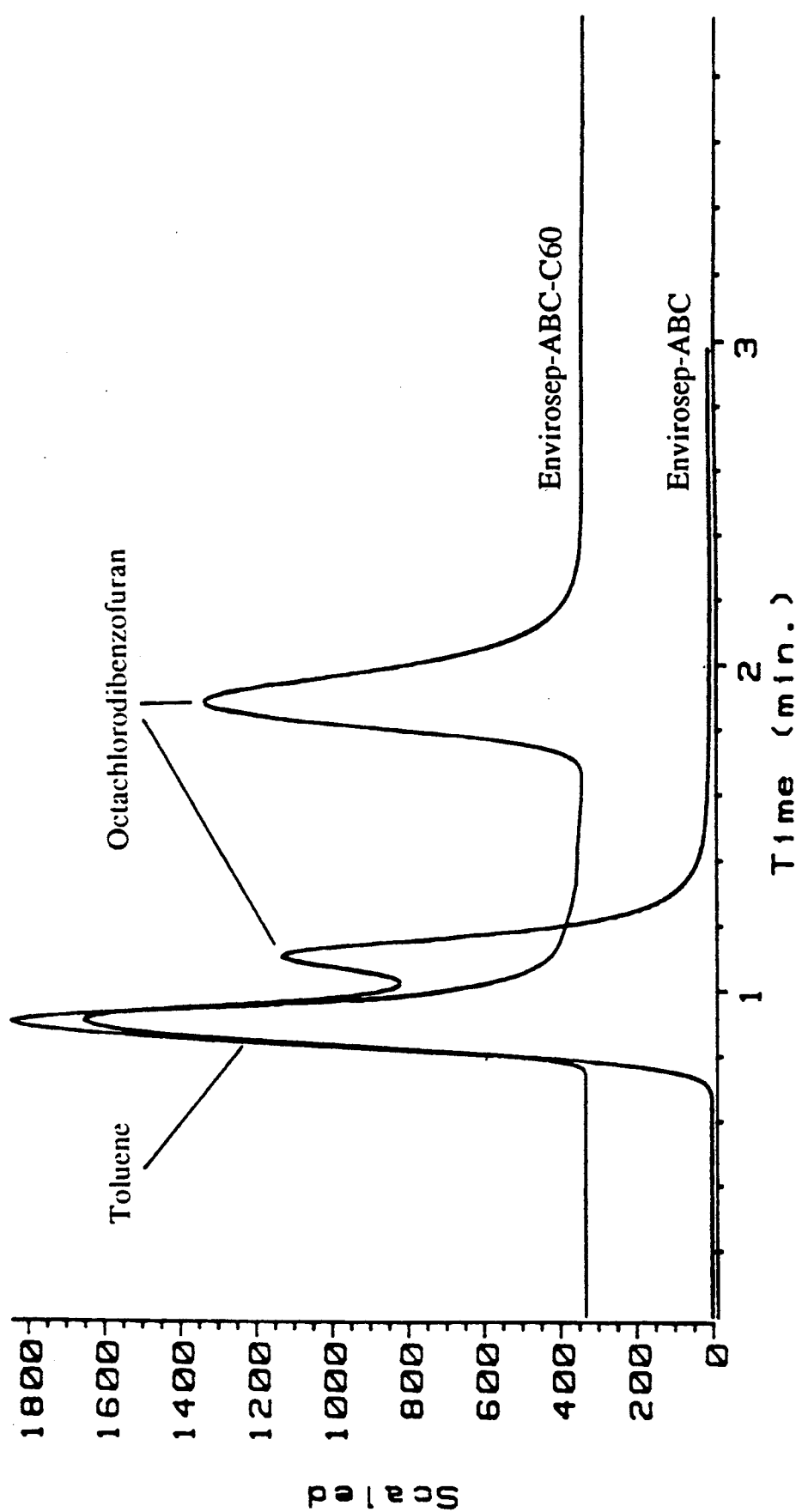

This product was then packed into a 100×1.35 mm column. To illustrate the enhanced separation power of this new packing material, and its application to a wide range of classes of compounds, the separation power of this column for fullerenes C$_{60}$ and C$_{70}$, as well as for polyaromatic hydrocarbons and furans was compared to that of a similar column packed with Envirosep-ABC beads. Mobile phase for both columns consisted of 0.2 ml/min. of 20/80 (V/V) isocratic methylene chloride/isooctane. The results are shown in FIGS. 12-14. It is evident that the EP—C$_{60/70}$H column shows superior separation power, and greater affinity and retention power for all three classes of compounds. These materials show great utility for separation of PNAS, PCBS, PCDFS, PCDDS, as well as aliphatic compounds from aromatics such as found in waste oils and other industrial materials.

EXAMPLE 4

Synthesis of Resin-C$_{60/70}$HBr

The Envirosep-ABC column packing (EP) can also be directly linked to C$_{60/70}$ via the following reaction:

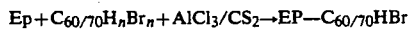

The synthesis procedure consists of first adding 0.2 g of EP (5 μm, 100 Å) 10 ml of CS$_2$, and 0.035 g of AlCl$_3$ to a 100 ml, three-neck flask equipped with condenser and stirrer. 0.021 g of C$_{60/70}$H$_n$Br$_n$ dissolved in 10 ml of CS$_2$ is then added under argon atmosphere. The reaction mixture is then stirred at room temperature for 24 hours.

After filtering, the solid product is successively washed with 6×2 ml of CS$_2$, 6×2 ml of H$_2$O, 9×2 ml of CH$_3$OH, 8×2 ml of toluene, 5×2 ml of CH$_2$Cl$_2$, 6×2 ml of THF, and 3×2 ml of ether. 0.192 g of a yellow-brown product is obtained.

EXAMPLE 5

Synthesis of Uniform Latex Particles with Surface Modification of Amino Groups Another method of synthesizing a PSDVB-NH$_2$ particle consists of first dissolving 0.098 g of SDS (dodecyl sulfate, sodium salt) and 0.02 g of NaHCO$_3$ in 26 ml of deionized water. After ultrasonication for 2 minutes, the solution was poured into a 100 ml three-neck flask equipped with condenser. 4 ml of styrene, 0.5 ml of divinylbenzene, 0.4 ml of 2-isopropenylaniline and 0.05 g of K$_2$S$_2$O$_8$ dissolved in 2 ml of deionized water was then added. The polymerization was conducted at 650° C. for 18 hr under Ar gas. The aqueous latex particles were then filtered. Twenty-eight ml of latex having a pH of 6.5 were obtained. After lyophilizing, a dry product consisting of particles with average diameter of 0.1 μm was obtained. These amino-group-containing particles are herein designated as (particle)-NH$_2$.

EXAMPLE 6

Synthesis of (Particle)-NH—(CH$_2$)$_8$O—C$_{60/70}$H$_x$Br$_{y-z}$-[O(CH$_2$)$_8$Br]$_{z-1}$

6(a) Synthesis of C$_{60/70}$H, from a Mixture of C$_{60}$ and C$_{70}$ and Subsequent Bromination To a 250 ml three-neck flask equipped with dry ice acetone condenser and stirrer, 25 ml of t-BuOH, a suspension of 70 mg of C$_{60/70}$ in 40 ml of anhydrous THF, and 80 ml of liquid ammonia were added. 150 mg (0.0216 mole) of lithium was then added. Following stirring for about 105 min., the color of the reaction mixture changed from dark black to light cream. The stirring was continued for 1 hr with reflux, and the ammonia was then allowed to evaporate at room temperature for about 3 hrs.

To the residue, 120 ml of water and 100 ml of ether were added. The solid product between the two layers was collected and washed with ether, and the ether layer was then centrifuged. Small amounts of product were obtained and combined with the above solid product. Total recovered product was 67.1 mg or 91.5% of estimated conversion. This reaction scheme is displayed in FIG. 1B, reaction (3).

Product Characterization

The analytical data for the recovered product were as follows:

Thin Layer Chromatography (TLC): $R_f = 0.38$, the spots were revealed with $I_2$, sample solvent $CH_2Cl_2$, developing reagent 30% $CH_2Cl_2$ in hexane, aluminum sheet silica gel 60 $F_{254}$.

$^1$H NMR:ppm (benzene-$d_6$): 7.37–6.95 (m), 5.25, 3.85 (m), 3.35 (m), 1.75 (s), 1.68 (s), 0.92 (s), 0.76 (m), 0.61 (s), 0.41 (m)

FAB-MS: $C_{60}H_{12}$ (m/z 731), $C_{60}H_{28}$ (m/z 747), $C_{60}H_{38}$ (m/z 757), $C_{60}H_{48}$ (m/z 767), $C_{70}H_{26}$ (m/z 865), $C_{70}H_{36}$ (m/z 875).

6(b) Bromination of $C_{60/70}H_x$

To a 100 ml three-neck flask equipped with an alcohol thermometer, a dropping funnel and a stirrer, 44 mg of $C_{60/70}H$, and 36 ml of mixing solution ($CH_2Cl_2/CHCl_3 = 1:1$ with volume) were added. After the forming suspension was stirred 10 min., the reaction flask was placed in a dry ice-acetone bath. When the temperature reached $-55°$ C., a solution of 0.015 ml (0.29 mmol) of bromine dissolved in 6 ml of mixing solution ($CH_2Cl_2/CHCl_3 = 1:1$ by volume) was added dropwise. The reaction mixture (red color) was then stirred for 1 hour at $-55°$ C.

The solvent was then evaporated under vacuum, and the residue was washed with ether. 63 mg of $C_{60/70}H_xBr_y$ product was obtained. This reaction is displayed in FIG. 1B, reaction (4).

The analytical data for the recovered product were as follows:

$^1$H NMR:ppm (CDCl$_3$): 7.75–7.55 (m), 4.45 (s), 4.20 (m), 3.75 (m), 2.45 (m), 1.58 (s), 1.25 (s), 0.90 (m).

$^{13}$C NMR:ppm (CDCl$_3$): 133, 131, 71, 42, 33, 32, 31, 26, 21, 19, 17, 13, 3.

FAB-MS: $CH_{60}H_{36}Br_6$(m/z 1236), $C_{60}H_{38}Br_4$ (m/z 1078), $C_{70}H_8Br_2$(m/z 1008).

6(c) Synthesis of $C_{60/70}H_xBr_{y-z}[O(CH_2)_8Br]_z$

First, 0.4 ml (0.0023 mole) of 8-bromo-1-octanol in 50 ml of abs. ether and 0.026 g (0.0015 mole) of Na granules were added to a 250 ml three-necked flask equipped with stirrer and condenser. The reaction mixture was then refluxed gently under Ar gas until Na reacted completely.

Thirty (30) mg of $C_{60/70}H_xBr_y$ in 36 ml abs. ether were then added to the reaction system, and the reaction mixture was refluxed continuously 24 hrs. 100 ml of water were then added. After stirring the mixture for 5 min., 15.4 mg of a brown colored solid were separated and recovered.

Product Characterization

The analytical data for the recovered product were as follows:

$^1$H NMR:ppm (CDCl$_2$): 5.38 (s), 4.30 (s), 4.03 (s), 3.65 (s), 3.38 (s), 2.43 (s), 2.35 (d), 1.82 (s), 1.51 (s), 1.38 (s), 1.30 (s), 1.25 (s), 0.90 (s).

$^{13}$C NMR: ppm (CDCl$_3$): 63.01, 33.97, 32.73, 32.71, 29.70, 29.65, 29.36, 29.20, 28.87, 28.79, 28.09, 26.63.

FAB-MS: $C_{60}H_{36}Br[O(CH_2)_8Br\ ]_3$(m/z 1459), $C_{60}H_2Br_2[O(CH_2)_8Br]_2$(m/z 1297), $C_{60}H_{36}Br[O(CH_2)_8Br]$(m/z 1043).

6 (d) Synthesis of (PSDVB Particle) -NH—(CH$_2$)$_8$O—C$_{60/70}$H$_x$Br$_{y-x}$[(CH$_2$)$_8$Br ]$_{x-1}$ First 5 mg of $C_{60/70}H_xBr_{y-z}[O(CH_2)_8Br]_z$ and 16 ml of ethylene glycol dimethyl ether were added into a 100 ml two-neck flask equipped with a stirrer. After stirring for 30 min., a latex suspension was added. The latex suspension was formed by mixing 11.2 mg of dry (PSDVB particle)-NH$_2$ in 5 ml of deionized water and ultrasonicating the suspension for 1 min. The pH of the latex suspension was adjusted from 5.28 to 8.40 with buffer. The reaction mixture (pH 9.73) was then stirred at room temperature for 19 hrs, and then filtered. A brown solid was collected from the filter paper.

Figure 1C:
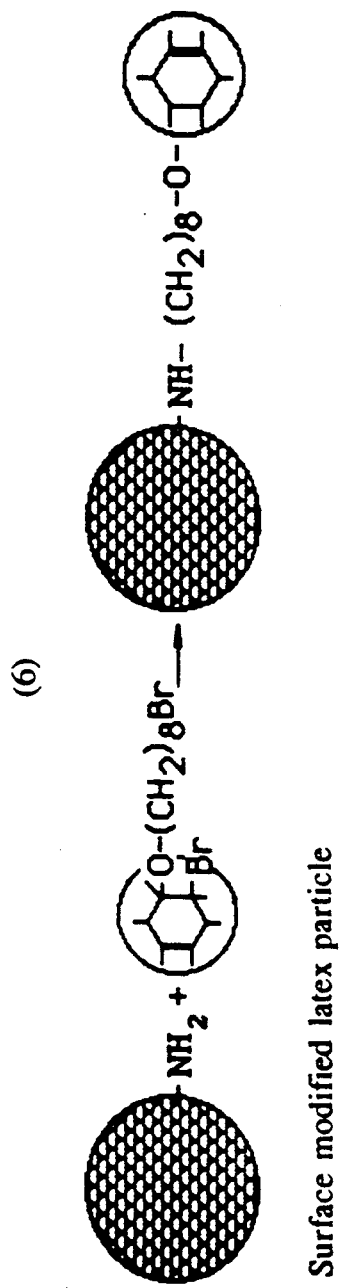
Figure 1C:
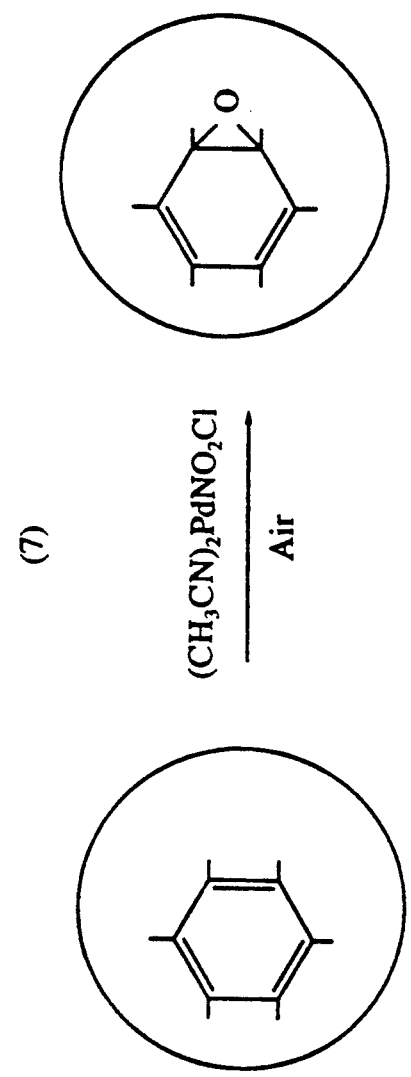

Solvent evaporation of the filtrate under vacuum, yielded a yellow residue. Both the brown solid and the yellow residue tested positive for aromatic amine. The reaction leading to this product is shown in FIG. 1C, reaction (6).

EXAMPLE 7

Oxidation of $C_{60/70}$

To a 125 ml flask, 0.45 g (0.0017 mol) of Pd(CH$_3$CN)$_2$Cl$_2$ suspended in 70 ml of CH$_3$CN and 0.2669 g (0.0017 mol) of silver nitrite dissolved in 28 ml of CH$_3$CN were added. AgCl was precipitated immediately. The reaction mixture was stirred at room temperature for 2.5 hrs. After filtration, the solvent was removed from the filtrate under vacuum. The cis-bis-(acetonitrile) chloronitropalladium product amounted to 0.398 of a yellow-orange solid (yield 86.76%) and was stored at 0° C. in a tightly closed bottle.

To a 100 ml flask, 0.05 g (0.00185 mol) of Pd(CH$_3$CN)$_2$NO$_2$Cl dissolved in 1.5 ml of CH$_2$Cl$_2$ and 0.010 g of C$_{60/70}$ dissolved in 10 ml of toluene, were added. The reaction mixture was then exposed to air supplied through a drying tube and stirred at room temperature of 263 hrs. The reaction process was monitored by HPLC. After centrifugation, the oxygen substituted C$_{60/70}$ product was collected. This reaction is depicted in FIG. 1C, reaction (7).

In an alternate procedure, 0.10 g (0.0037 mol) of Pd(CH$_3$CN)$_2$NO$_2$Cl dissolved in 30 ml of CH$_2$Cl$_2$ and 0.020 g of C$_{60/70}$ were added to a 100 ml flask. The reaction mixture was exposed to air supplied through a drying tube and was stirred at room temperature for 304 hrs. The reaction process was monitored by HPLC. The recovered oxygen-substituted C$_{60/70}$ solid product bore a black color.

EXAMPLE 8

The following is a description of other reactions leading to chromatographic materials based on C$_{60/70}$ linked to silica support.

Synthesis of Bi—NHC$_{60}$H

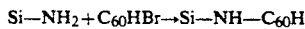

First, 0.4 g of 5 gm O.D. spherical particles of silica gel with amino group (Spherisorb, Phenomenex Inc., Torrance, Calif.) in 8 ml of toluene, 0.065 g of C$_{60}$HBr in 8 ml of toluene, and 0.2 ml of saturated NaHCO$_3$ solution were poured into a 100 ml three-neck flask. Following stirring for 23 hours at 34° C. in an argon atmosphere, the reaction mixture was refluxed for 45 hours. The reaction mixture was then centrifuged at room temperature, and the solid product was washed with toluene until no yellow color was observed in the wash solution. Any excess $C_{60}HBr$ reactant remaining in the product was thereby removed. The $Si-NH-C_{60}H$ product bore a yellow-brown color.

Product Characterization

Figure 15:
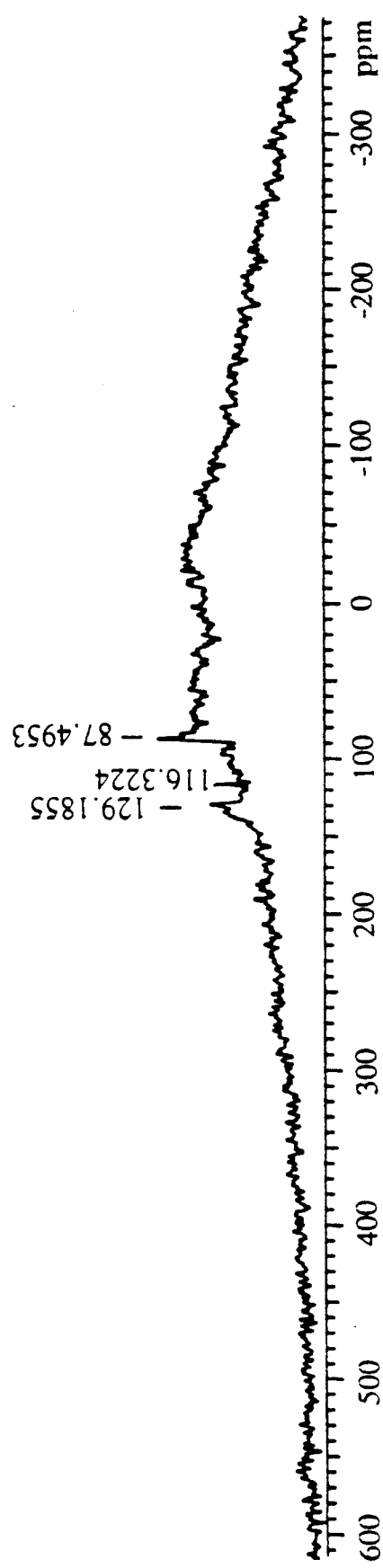
FIGS. 15, 16A, 16B, 16C and 17 display properties of products produced in Example 8.

Magic Angle Spinning $^{13}C$-NMR: FIG. 15 shows the spectrum of the reaction product ($Si-NH-C_{60}H$) obtained by magic angle spinning $^{13}C$-NMR. Signals at 129 ppm and 116 ppm are for $C_{60}$'s carbon double bond and signal at 87 ppm was for $C_{60}$'s single carbon bond $C-NH$. This determination confirms that $C_{60}$'s is attached to the amine group of the silica support.

Figure 16A:
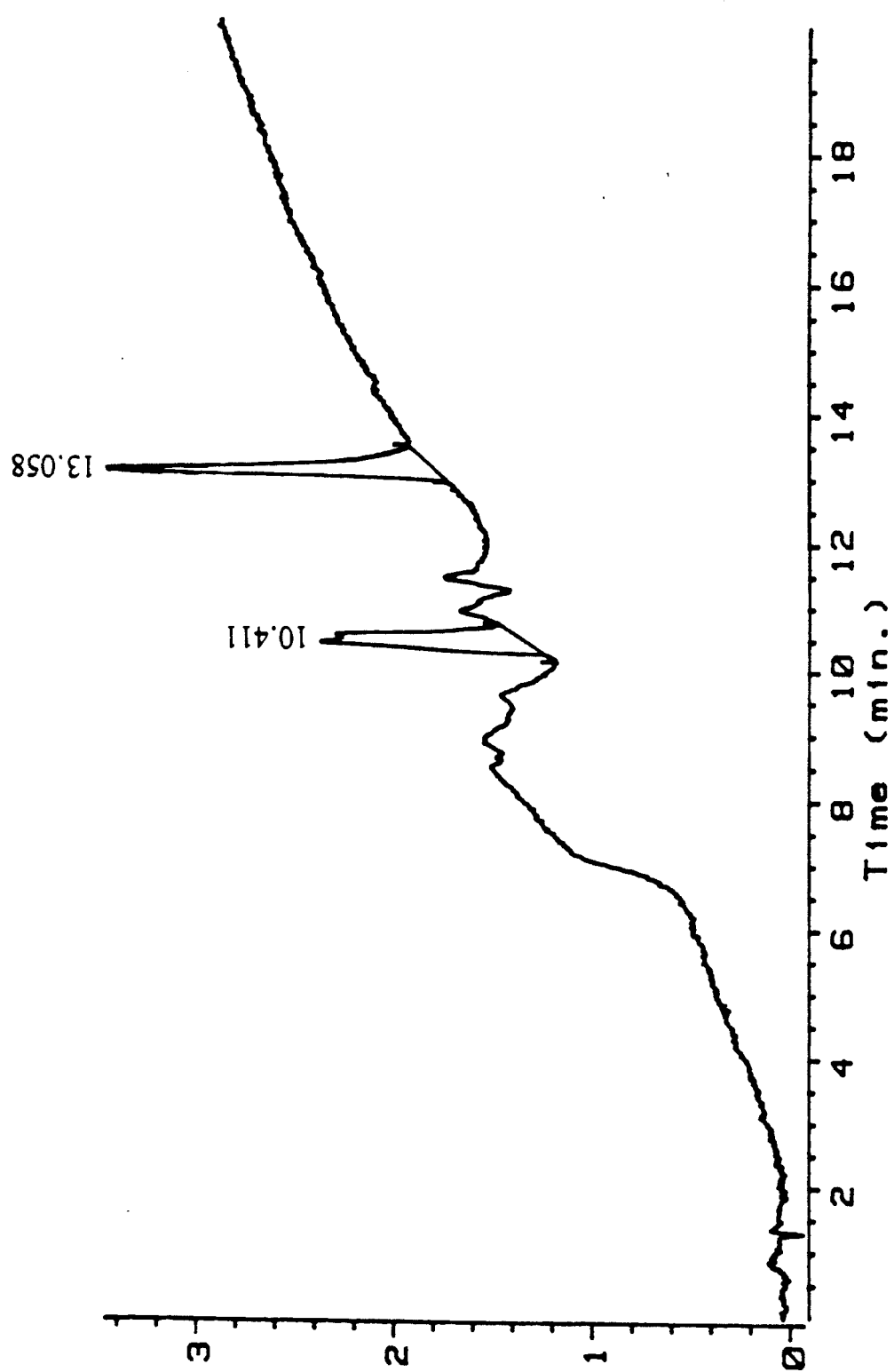

PCB Adsorption Test: FIG. 16A shows the HPLC chromatogram of a solution of 0.51 μg of PCB in 1 ml of cyclopentane. The area of the PCB peak is 19 units.

Figure 16B:
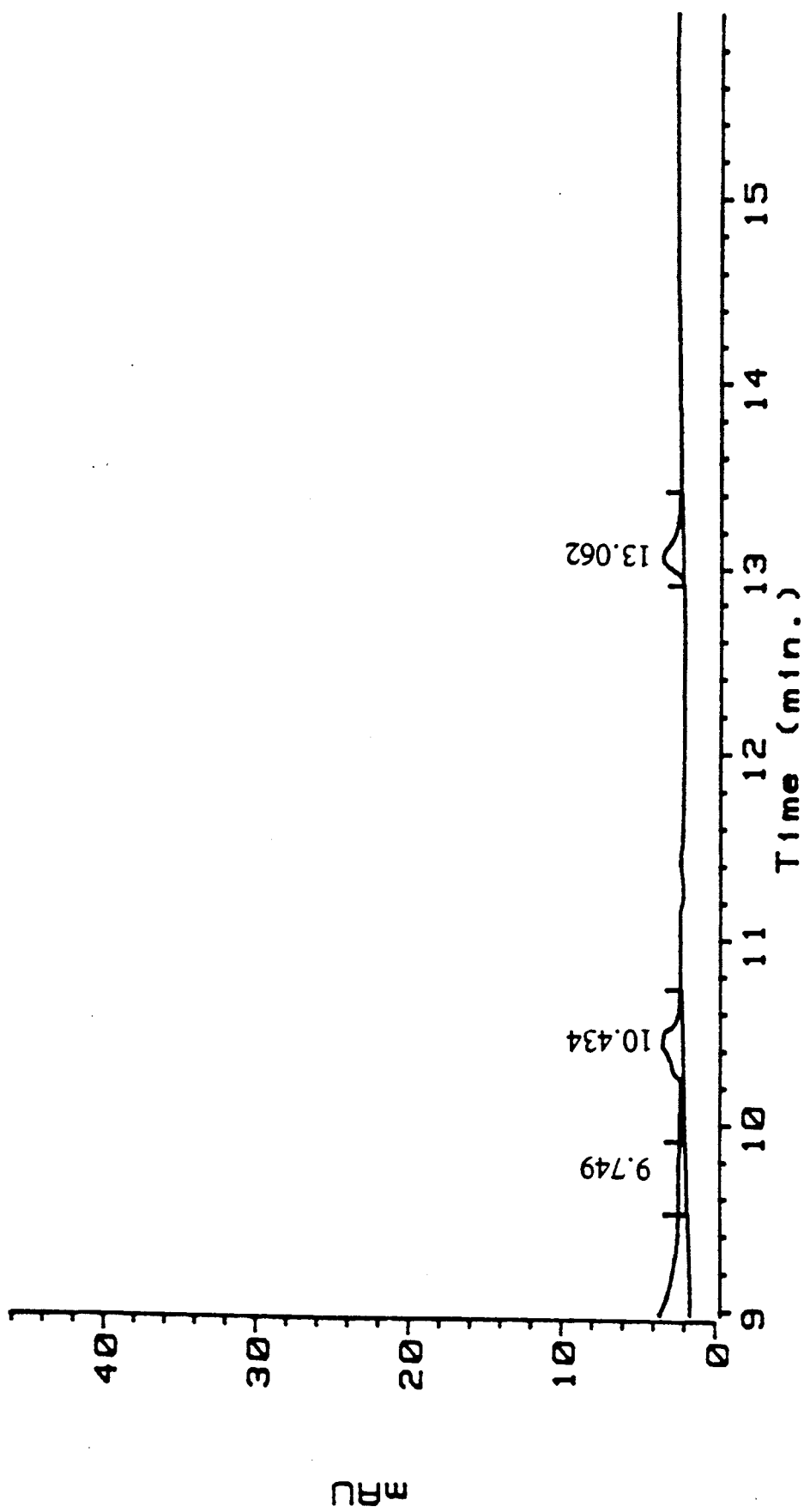

FIG. 16B shows the HPLC chromatogram of the supernatant solution of 0.2 g of silica-$NH_2$ and 0.51 μg PCB in 1 ml of cyclopentane. The area of the PCB is 17 units.

Figure 16C:
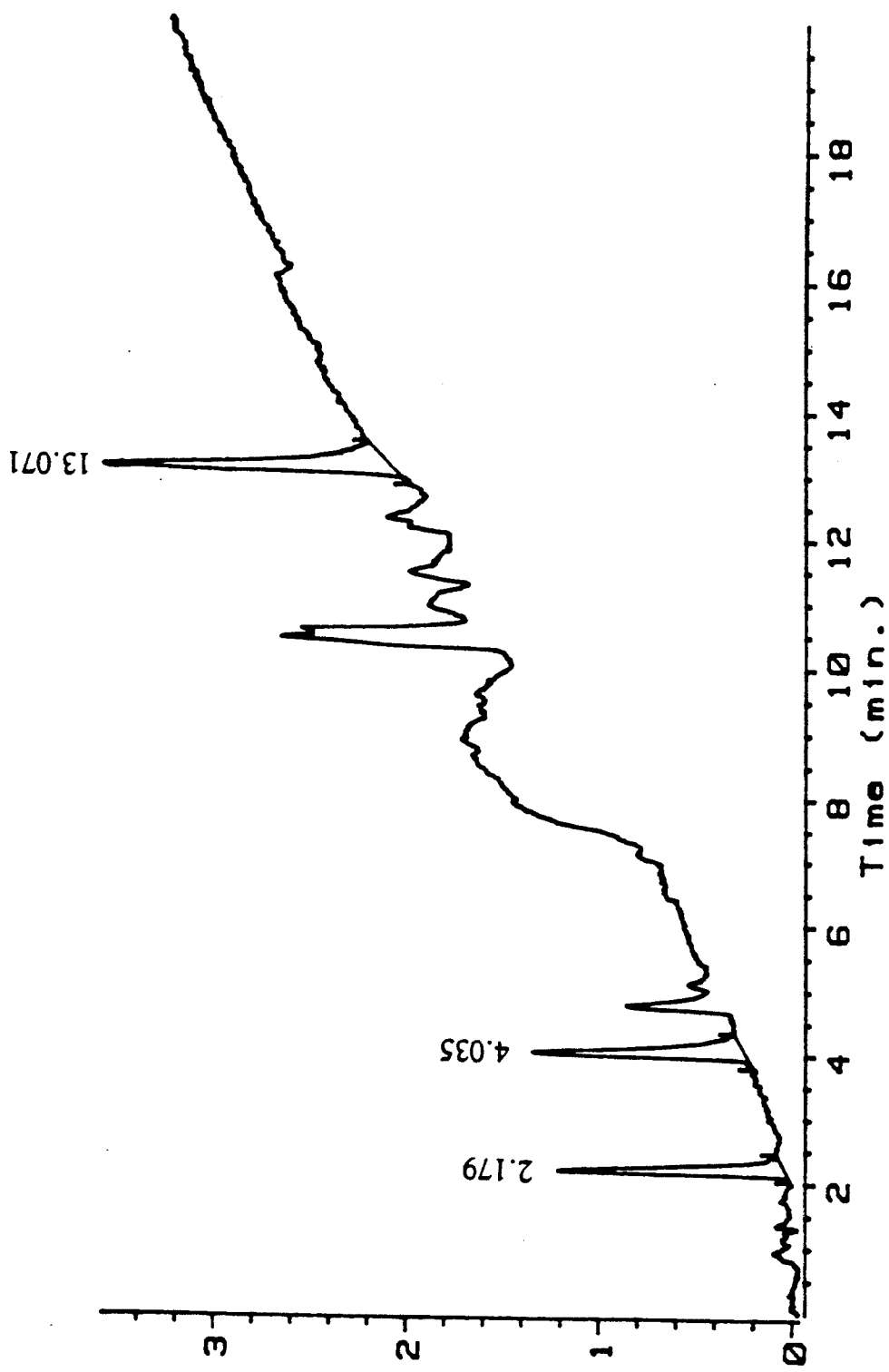

FIG. 16C shows the HPLC chromatogram of the supernatant solution of 0.226 g of the reaction product and 0.51 μg of PCB in 1 ml of cyclopentane. The area of the PCB is 14 units.

The reaction product thus has a greater adsorption capacity for the aromatic PCB than the $Si-NH$, particles. This test confirms that the reaction product has more affinity towards aromatic compounds than the $Si-NH_2$ reactant.

The reaction product, $Si-NH-C_{60}H$, was dry-packed into a 50 mm long, 2.1 mm I.D., ⅛" O.D. stainless steel column, and fitted at both ends with Upchurch (Oak Harbor, Wash.) microcolumn fittings and 0.5 μm filter frits.

A 20/80 $H_2OCH_3CN$ (V/V) reverse phase mixture was used as elution solvent. The column temperature was 40° C. and elution solvent flow rate was 0.4 ml/min. Analytes were detected using an HP-1040 photodiode array detector (Hewlett-Packard Co., Avondale, Pa.).

Figure 17:
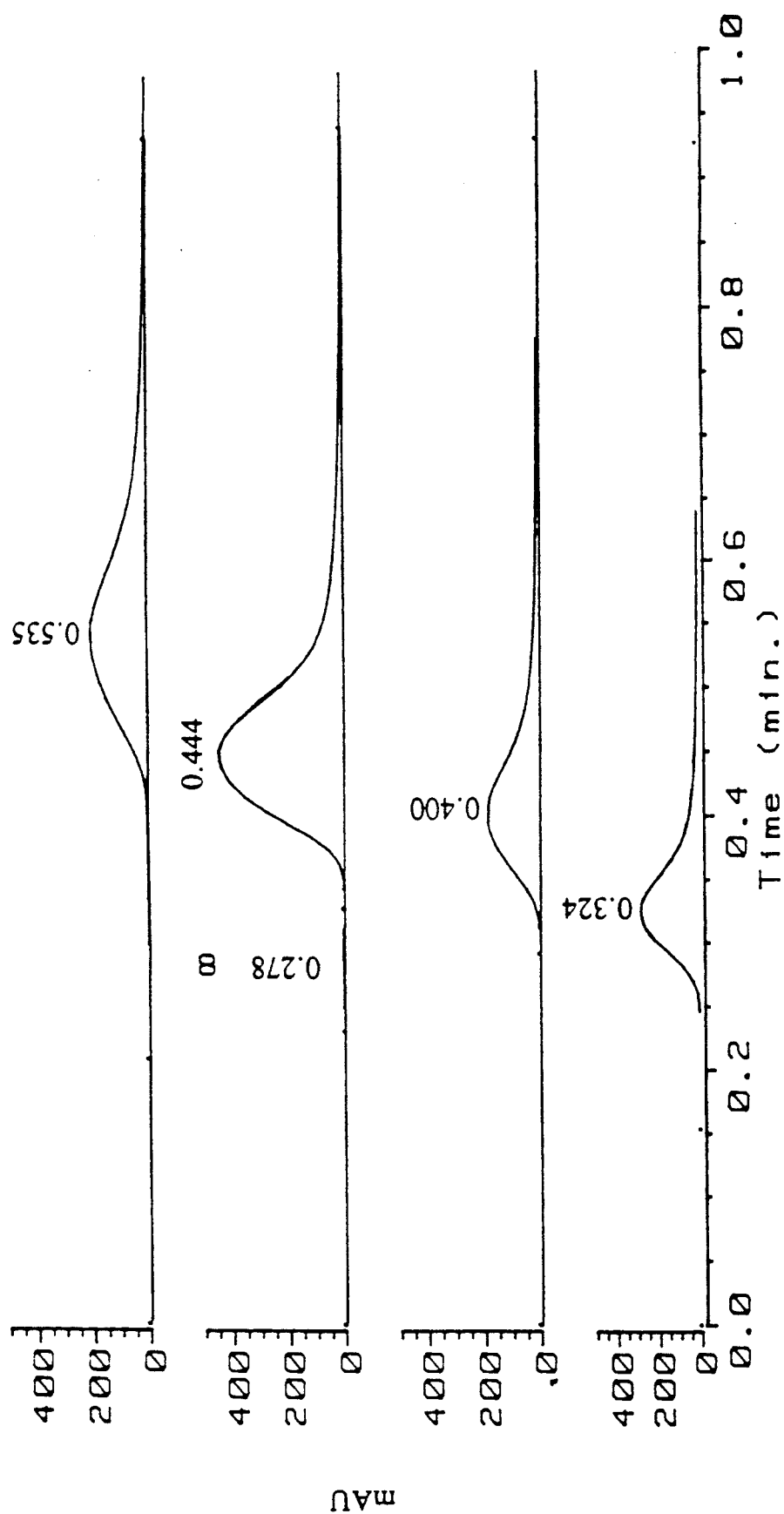

Chromatography of PCBs: The following polychlorinated biphenyls (PCBS) were obtained from Accustandard (New Haven, Conn.): 2,2',6,6'; 3,3',4,4'; 3,3',4,4',5 ; 3,3',4,4',5,5'. FIG. 17 illustrates a separation of PCBs on $Si-NH-C_{60}H$ stationary phase. Separation of the PCBs on the $Si-NH-C_{60}H$ is evident, demonstrating the ability of this column to separate PCBS. This column shows increased affinity with increased planarity and degree of chlorination of the PCB molecules, and may be used for separation of a variety of other compounds such as PNAS, PCDFS, and PCDDS.

EXAMPLE 9

Synthesis of $Si-NH(CH_2)_8OC_{60}H$

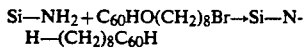

First, 0.6 g of silica gel with amino group in 18 ml of benzene, 0.17 g of $C_{60}HO(CH_2)_8Br$ dissolved in 2 ml of benzene, and 0.17 g of $K_2CO_3$ were combined in a 50 ml three-neck flask. Following stirring for 2 hours at room temperature in an argon atmosphere, the reaction mixture was refluxed for 51 hours. The reaction mixture was then centrifuged at room temperature to separate $K_2CO_3$ from the reaction product, and the solid product was washed with benzene until no yellow color was observed in the wash solution. Any excess $C_{60}HO(CH_2)_8BR$ reactant remaining in the product was thus removed.

EXAMPLE 10

Synthesis of Silica-X—Si—$R_2$—$C_6H_4$—$C_{60/70}H$ or Silica-X—SiR—($C_6H_4$—$C_{60/70}H)_2$ Fullerenes can be directly attached to an organosilane functionalized porous or non-porous silica particle/bead as follows:

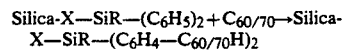

where X represents an inorganic or organic linking moiety such as $Si-O-Si-R$ or $-(CH_2)_{n-}$ where n=1 to 4 between the silica network and the terminal aromatic organosilane group and R designates an organic functional group attached to the terminal organosilane atom.

The synthesis procedure consists of first adding 0.2 g of Diphenylmethylsilane functionalized silica gel (10 μm, 100 Å) in 8 ml of $CS_2$, and 0.09 g of $AlCl_3$ to a 50 ml, three-neck flask equipped with condenser and stirrer. 0.05 g of $C_{60/70}$ dissolved in 15 ml of $CS_2$ is then added under argon atmosphere. The reaction mixture is then stirred at room temperature for 42 hours.

After filtering, the solid product is successively washed with 6×2 ml of $CS_2$, 6×2 ml of $H_2O$, 6×2 ml of $CH_3OH$, 5×2 ml of toluene, 4×2 ml of $CH_2Cl_2$, 3×2 ml of THF, and 4×2 ml of ether. A yellow-brown product is obtained. In reacting some functionalized silane materials, a less acidic catalyst may be advantageous, e.g. $BF_3$ or $FeCl_3$.

The Described materials in all 10 examples can be used in a variety of applications, including the separation of PNAS, PCBS, PCDFS, PCDDS, as well as aliphatic and other compounds from aromatics such as found in waste oils and other industrial materials. Although the invention has been described with regard to certain preferred embodiments, it should be understood that such modifications as would be obvious to one having skill in the art may be made without deviating from the scope of the invention which is defined by the appended claims.

We claim:

1. A support particle suitable for use in chromatographic separations having a buckminsterfullerene covalently bound thereto, said particle being porous or non-porous, having an average particle diameter between about 0.1 micron and about 100.0 microns and being either directly covalently, bonded to the buckminsterfullerene, or having one or more functional groups covalently bonded by reaction with one or more pendant reactive groups of said buckminsterfullerene to bond said buckminsterfullerene to said particle.

2. The support particle as defined in claim 1 wherein said particle is a polymer particle.

3. The polymer particle as defined in claim 2 wherein said polymer particle or a coating on the polymer particle comprises the polymerization product of a vinyl-aromatic monomer and a divinyl aromatic monomer and an amino functional olefinic monomer.

4. The support particle as defined in claim 1 wherein said support particle comprises a polymer particle having an inner core of a polymer imparting dispersibility and stability to form said inner core of said particle and an outer shell of a different polymer over said shell containing at least one functional group reactive with said reactive groups of said buckminsterfullerene.

5. The support particle as defined in claim 1 wherein said particle comprises siliceous particle.

6. The support particle of claim 5 wherein the siliceous particle is selected from talc, kaolinite, pyrophyllite, serpentine, smectile, montmorillonite, mica, vermiculite, silica powder, porous glass, kieselguhr or diatomaceous earth.

7. The support particle as defined in claim 1 wherein said support particle is covalently bonded to said buckminsterfullerene, or a spacer compound is covalently bonded between said support particle and said buckminsterfullerene.

8. The support particle of claim 7 wherein $X_1$ and $X_2$ are independently selected from the group consisting of $NH_2$, $OH$, $COOH$, oxirano or halo groups.

9. The support particle as defined in claim 7 wherein said spacer compound is of the formula:

$$X_1-Z-X_2$$

wherein Z is a spacing unit and $X_1$ is a first functional group reactive with the functional groups on said support particle and $X_2$ represents a second functional group reactive with the functional groups on said buckminsterfullerene.

10. The support particle of claim 9 wherein the spacer compound is selected from the group consisting of:

$X_1-(CH_2)_n-X_2$;
$X_1-OC-(CH_2)_n-CO-X_2$, $X_1-CH_2-C_6H_4-CH_2-X_2$ or

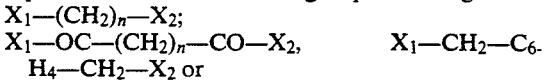

and n = 2 to 17.

11. The support particle of claim 10 wherein $X_1$ and $X_2$ are independently selected from the group consisting of $NH_2$, $OH$, $COOH$, oxirano or halo groups.

12. A self-supporting silica matrix which comprises the material of claim 1.

13. The support particle of claim 1 wherein said particle is porous having a pore size ranging between 10 to 50,000 Å.

* * * * *